(12) United States Patent
Medoff

(10) Patent No.: US 9,687,810 B2
(45) Date of Patent: *Jun. 27, 2017

(54) PROCESSING MATERIALS WITH ION BEAMS

(71) Applicant: XYLECO, INC., Wakefield, MA (US)

(72) Inventor: Marshall Medoff, Brookline, MA (US)

(73) Assignee: XYLECO, INC., Wakefield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/178,958

(22) Filed: Jun. 10, 2016

(65) Prior Publication Data

US 2016/0279591 A1    Sep. 29, 2016

Related U.S. Application Data

(63) Continuation of application No. 13/434,701, filed on Mar. 29, 2012, now Pat. No. 9,387,454, which is a
(Continued)

(51) Int. Cl.
*B01J 19/08* (2006.01)
*B01J 19/10* (2006.01)
(Continued)

(52) U.S. Cl.
CPC .......... *B01J 19/081* (2013.01); *B01J 19/085* (2013.01); *B01J 19/10* (2013.01); *B01J 19/12* (2013.01);
(Continued)

(58) Field of Classification Search
CPC ........ B01J 19/081; B01J 19/085; B01J 19/12; B01J 19/10; B01J 2219/0879; C10L 9/00; C10L 5/44; H01J 37/04; H01J 37/05
(Continued)

(56) References Cited

U.S. PATENT DOCUMENTS 2,895,891 A    6/1959  Miller
2,896,922 A    7/1959  Pohlman
(Continued)

FOREIGN PATENT DOCUMENTS

JP    2007-175540    7/2007
KR    10-0873700    12/2008
(Continued)

OTHER PUBLICATIONS

Ershov, B.G., "Radiation-Chemical Degradation of Cellulose and Other Polysaccharides," Russian Chemical Reviews, 67(4) 315-334 (1998).
(Continued)

*Primary Examiner* — Keith Hendricks
*Assistant Examiner* — Colleen M Raphael
(74) *Attorney, Agent, or Firm* — Leber IP Law

(57) ABSTRACT

Materials such as biomass (e.g., plant biomass, animal biomass, and municipal waste biomass) and hydrocarbon-containing materials are processed to produce useful products, such as fuels. For example, systems are described that can use feedstock materials, such as cellulosic and/or lignocellulosic materials and/or starchy materials, or oil sands, oil shale, tar sands, bitumen, and coal to produce altered materials such as fuels (e.g., ethanol and/or butanol). The processing includes exposing the materials to an ion beam.

33 Claims, 6 Drawing Sheets

Related U.S. Application Data continuation of application No. 12/486,436, filed on Jun. 17, 2009, now Pat. No. 8,147,655.

(60) Provisional application No. 61/073,680, filed on Jun. 18, 2008.

(51) Int. Cl.
| | | |
|---|---|---|
| *B01J 19/12* | (2006.01) | |
| *C10L 9/00* | (2006.01) | |
| *H01J 37/04* | (2006.01) | |
| *H01J 37/05* | (2006.01) | |
| *C10L 5/44* | (2006.01) | |

(52) U.S. Cl.
CPC ............... *C10L 9/00* (2013.01); *H01J 37/04* (2013.01); *H01J 37/05* (2013.01); *B01J 2219/0879* (2013.01); *C10L 5/44* (2013.01); *Y02E 50/30* (2013.01)

(58) Field of Classification Search
USPC ........................................ 204/157.63, 157.15
See application file for complete search history.

(56) References Cited

U.S. PATENT DOCUMENTS

| | | | |
|---|---|---|---|
| 3,006,831 | A | 10/1961 | Illman |
| 3,107,206 | A | 10/1963 | Clement |
| 4,751,170 | A | 6/1988 | Mimura et al. |
| 4,769,082 | A | 9/1988 | Kumakura et al. |
| 4,956,219 | A | 9/1990 | Legras et al. |
| 5,128,543 | A | 7/1992 | Reed et al. |
| 5,374,318 | A * | 12/1994 | Rabalais ............ C30B 23/02 427/561 |
| 5,473,165 | A | 12/1995 | Stinnett et al. |
| 5,532,495 | A | 7/1996 | Bloomquist et al. |
| 5,900,443 | A | 5/1999 | Stinnett et al. |
| 6,315,871 | B1 | 11/2001 | Daulton et al. |
| 6,638,895 | B1 | 10/2003 | Karapetrov et al. |
| 2004/0000650 | A1 * | 1/2004 | Yanagisawa ............ G21K 5/04 250/492.3 |
| 2004/0129394 | A1 | 7/2004 | Graveson |
| 2006/0076510 | A1 * | 4/2006 | Chang ............ H01J 37/3171 250/492.21 |
| 2006/0145088 | A1 | 7/2006 | Ma |
| 2008/0067452 | A1 | 3/2008 | Moriyama |
| 2008/0313954 | A1 | 12/2008 | Lee |
| 2012/0305384 | A1 | 12/2012 | Zalkin et al. |

FOREIGN PATENT DOCUMENTS

| | | |
|---|---|---|
| RU | 2071992 | 1/1997 |
| RU | 2154654 | 8/2000 |
| WO | 0126569 | 4/2001 |
| WO | 2008014526 | 1/2008 |

OTHER PUBLICATIONS

Eurasian Search Report, Eurasian Application No. 201401307, dated Apr. 14, 2015, 2 pages.
Seymour and Carraher, Polymer Chemistry: An Introduction, 3rd ed., Marcel Dekker Inc., 1992, chapter 15, p. 420, para. 7, lines 1-6.
Abstract of JP 2007-175540A, Patent Abstracts of Japan, 1 page.
Moroz et al., "Optical Alteration of Complex Organics Induced by Ion Irradiation: 1. Laboratory Experiments Suggest Unusual Space Weathering Trend," Icarus, Elsevier, [Online] vol. 170, Mar. 24, 2004, pp. 214-228, XP002557447.
Dong et al., "The Influence of Carbon Ion Irradiation on Sweet Sorghum Seeds," Nuclear Instruments and Methods in Physics Research, Section B: Beam Interactions with Materials and Atoms, Elsevier, Amsterdam, NL, vol. 266, No. 1, Nov. 1, 2007, pp. 123-126, XP022409319.
ISR and Written Opinion for PCT/US2009/047650, WIPO, 15 pp., mailed Dec. 9, 2009.
Rajasekaran et al., "Interlayer Carbon Bond Formation Induced by Hydrogen Adsorption in Few-Layer Supported Graphene," Phys. Rev. Lett. 111, 085503 (Aug. 23, 2013).
Zekonyte et al., "Mechanisms of Argon Ion-Beam Surface Modification of Polystyrene," Surface Science (2003), vol. 532-535, pp. 1040-1044.
Ermer et al., "Deuterium Depth Profiling in Polymers Using Heavy Ion Elastic Recoil Detection," Nuclear Instruments and Methods in Physics Research B, vol. 134 (1998), pp. 237-248.
Lee et al., "Microstructure and Adhesion of Au Deposited on Parylene-c Substrate with Surface Modification for Potential Immunoassay Application," IEEE Transactions on Plasma Science, vol. 32, No. 2, Apr. 2004.

* cited by examiner

PROCESSING MATERIALS WITH ION BEAMS

RELATED APPLICATIONS

This application is a continuation of U.S. Ser. No. 13/434,701, filed Mar. 29, 2012, which is a continuation of U.S. Ser. No. 12/486,436, filed Jun. 17, 2009, now U.S. Pat. No. 8,147,655 granted on Apr. 3, 2012, which claims priority to U.S. Provisional Application Ser. No. 61/073,680, filed Jun. 18, 2008. The complete disclosure of each of these applications is hereby incorporated by reference herein.

BACKGROUND

Biomass, particularly biomass waste, and hydrocarbon-containing materials, such as oil sands, oil shale, tar sands, bitumen, and coal, are widely available. It would be useful to derive materials and fuel, such as ethanol, from biomass and hydrocarbon-containing material.

SUMMARY

Biomass and hydrocarbon-containing material can be processed to alter its structure at one or more levels. The processed materials can then be used as a source of altered materials and/or fuel.

Many embodiments of this application use Natural Force™ Chemistry (NFC). Natural Force™ Chemistry methods use the controlled application and manipulation of physical forces, such as particle beams, gravity, light, etc., to create intended structural and chemical molecular change.

Methods for changing a molecular and/or a supramolecular structure of a material, e.g., any biomass material, can include treating the material with radiation. In particular, the radiation can include particles, particularly charged particles (e.g., accelerated charged particles). Charged particles include ions, such as positively charged ions, such as protons, carbon or oxygen ions. The radiation can be applied in an amount sufficient to change the molecular structure and/or supramolecular structure of the material. The radiation can also be applied to produce one or more products from the material. The material can in some cases include carbohydrates or materials that include carbohydrates, e.g., cellulosic materials, lignocellulosic materials, starchy materials, or mixtures of any biomass materials.

Particles having a different charge than electrons and/or particles heavier than electrons can be utilized for the irradiation. For example, protons, helium nuclei, argon ions, silicon ions, neon ions, carbon ions, phosphorus ions, oxygen ions or nitrogen ions can be utilized to modify the structure of the biomass, e.g., breakdown the molecular weight or increase the molecular weight of the biomass. In some embodiments, heavier particles can induce higher amounts of chain scission in comparison to electrons or photons. In addition, in some instances, positively charged particles can induce relatively large amounts of chain scission due to their acidity. In certain instances, negatively charged particles can induce relatively large amounts of chain scission due to their alkalinity.

Accordingly, in one aspect, the invention features a method of changing a molecular structure of a material, e.g., a biomass material or a hydrocarbon-containing material, by producing an ion beam comprising a first distribution of ion energies having a full width at half maximum of w; adjusting the energies of at least some of the ions to produce a second distribution of ion energies in the ion beam having a full width at half maximum of more than w; and exposing the material to the adjusted ion beam. The energies of at least some of the ions can be adjusted based on, for example, a thickness of the material.

In another aspect, the invention features a method of changing a molecular structure of a material, e.g., a biomass material or a hydrocarbon-containing material, by producing an ion beam comprising a distribution of ion energies having a full width at half maximum of w; directing the ion beam to pass through a scattering element configured to increase the full width at half maximum of the distribution of ion energies to a value larger than w; and exposing the material to the ion beam after the ion beam has passed through the scattering element.

In yet another aspect, the invention features a method of changing a molecular structure of a material, e.g., a biomass material or a hydrocarbon-containing material, by producing an ion beam having a distribution of ion energies, the distribution having a most probable energy E; filtering the ion beam to remove at least some ions having an energy less than E from the ion beam; and exposing the material to the filtered ion beam.

In a further aspect, the invention features a method of changing a molecular structure of a material, e.g., a biomass material or a hydrocarbon-containing material, by producing an ion beam having a distribution of ion energies; adjusting the distribution of ion energies based on an expected ion dose profile in the material; and exposing the material to the adjusted ion beam.

The invention also features a method of changing a molecular structure of a material, e.g., a biomass material or a hydrocarbon-containing material, by producing an ion beam having a distribution of ion energies; adjusting the distribution of ion energies based on a full width at half maximum (FWHM) of a Bragg peak of an expected ion dose profile in the material; and exposing the material to the adjusted ion beam, wherein the adjusting comprises increasing the FWHM to reduce a difference between a thickness of the biomass material and the FWHM.

In some cases, following the adjusting, the difference between the thickness of the material and the FWHM is 0.01 cm or less.

In yet another aspect, the invention features a method of changing a molecular structure of a material by producing a first ion beam from an ion source, the first ion beam having a first average ion energy; exposing the material to the first ion beam; adjusting the ion source to produce a second ion beam having a second average ion energy different from the first average ion energy; and exposing the material to the second ion beam.

In some cases, the method further includes repeating the adjusting and exposing to expose the material to a plurality of ion beams having different average ion energies. The composition of the first and second ion beams can be the same.

In a further aspect, the invention features a method of changing a molecular structure of a material by:

producing a first ion beam from an ion source, the first ion beam having a first average ion energy corresponding to a first position of a Bragg peak in an expected ion dose profile of the material;

exposing the material to the first ion beam;

adjusting the ion source to produce a second ion beam having a second average ion energy corresponding to a second position of the Bragg peak different from the first position; and exposing the material to the second ion beam.

In some cases, the method further includes repeating the adjusting and exposing to expose the material to a plurality of ion beams corresponding to different positions of the Bragg peak. The composition of the first and second ion beams can be the same.

In yet another aspect, the invention features a method of changing a molecular structure of a material by producing an ion beam from an ion source, the ion beam comprising a first type of ions and a second type of ions different from the first type of ions; and exposing the material to the ion beam.

For example, the first type of ions can comprise hydrogen ions and the second type of ions can comprise carbon ions, or the first type of ions can comprise hydrogen ions and the second type of ions can comprise oxygen ions, or the first and second types of ions can comprise at least one of protons and hydride ions. In some cases the first and second types of ions each have ion energies between 0.01 MeV and 10 MeV.

In another aspect, the invention features a method of changing a molecular structure of a material by producing a ion beam having a divergence angle of 10 degrees or more, e.g., 20 degrees or more, at a surface of the material; and exposing the biomass material to the ion beam.

In yet another aspect, the invention features a method of changing a molecular structure of a material by adjusting an ion source to produce an ion beam having an average ion current and an average ion energy; and exposing the material to the ion beam, wherein the ion source is adjusted based on an expected ion dose profile in the material and wherein each portion of the material receives a radiation dose of between 0.01 Mrad and 50 Mrad, e.g., between 0.1 Mrad and 20 Mrad, as a result of exposure to the ion beam.

In another aspect, changing a molecular structure of a material includes producing an ion beam including a first distribution of ion energies having a full width at half maximum of W, adjusting the energies of at least some of the ions based on a thickness of a hydrocarbon-containing material to produce a second distribution of ion energies in the ion beam having a full width at half maximum of more than W, and exposing the hydrocarbon-containing material to the adjusted ion beam. The hydrocarbon-containing material can be selected from the group consisting of oil sands, oil shale, tar sands, bitumen, and coal.

In another aspect, changing a molecular structure of a material includes producing an ion beam including a first distribution of ion energies having a full width at half maximum of W, adjusting the energies of at least some of the ions to produce a second distribution of ion energies in the ion beam having a full width at half maximum of more than W, and exposing the material to the adjusted ion beam.

In some instances, the material is a biomass material, a non-biomass material, or any combination thereof. For example, the material can be a hydrocarbon-containing material such as oil sands, oil shale, tar sands, bitumen, coal, and other mixtures of hydrocarbons and non-hydrocarbon material.

In some cases, the method further includes exposing the material to a plurality of electrons or to ultrasonic energy following exposure to the ion beam.

Some implementations of any of the above-mentioned aspects of the invention can include one or more of the following features. Adjusting the energies of at least some of the ions can include adjusting based on a thickness of the material exposed to the ion beam. In some cases, adjusting the energies of at least some of the ions can include adjusting based on an expected ion dose profile in the material. Adjusting can also include increasing a full width at half maximum of a Bragg peak of an expected ion dose profile in the material enough to reduce a difference between a thickness of the material and the full width at half maximum of the Bragg peak. Following adjusting, the difference between the thickness of the material and the full width at half maximum of the Bragg peak can be 0.01 centimeter or less.

The full width at half maximum of the second distribution can be larger than w by a factor of 2.0 or more, e.g., by a factor of 4.0 or more. Adjusting the energies of at least some of the ions can include directing the ions to pass through a scattering element, e.g., a hemispherical analyzer. In some cases, the adjusted ion beam passes through a fluid prior to being incident on the material, e.g. through air at a pressure of 0.5 atmospheres or more. The ion beam can include two or more different types of ions, e.g., hydrogen ions and carbon ions or hydrogen ions and oxygen ions. The ion beam can include at least one of protons and hydride ions. The average energy of the ions in the ion beam can be between 0.01 MeV and 10 MeV.

Changing a molecular structure of a material, such as a biomass feedstock or a hydrocarbon-containing material, as used herein, means changing the chemical bonding arrangement, such as the type and quantity of functional groups or conformation of the structure. For example, the change in the molecular structure can include changing the supramolecular structure of the material, oxidation of the material, changing an average molecular weight, changing an average crystallinity, changing a surface area, changing a degree of polymerization, changing a porosity, changing a degree of branching, grafting on other materials, changing a crystalline domain size, or changing an overall domain size.

Biomass or hydrocarbon-containing material can be exposed to radiation, for example an ion beam, e.g., a beam according to one or more of the configurations described herein. The beam and duration of exposure can be chosen such that the molecular structure of the material is altered. The material can be treated prior to and/or after the exposure. The exposed material can be used in a variety of applications, including fermentation and the production of composite materials.

Also featured are systems and devices for treating materials with radiation as disclosed herein. An exemplary system includes a reservoir for biomass, a device that produces a particle beam, e.g., as described herein, and a conveyance device for moving biomass from the reservoir to the device that produces a particle beam.

Implementations may include one or more of any of the features described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

This application incorporates by reference herein the entire contents of International Application No. PCT/US2007/022719, filed Oct. 26, 2007, and U.S. Provisional Application No. 61/049,406, filed Apr. 30, 2008.

Other features and advantages will be apparent from the following detailed description, and from the claims.

DESCRIPTION OF DRAWINGS

Like reference symbols in the various drawings indicate like elements.

DETAILED DESCRIPTION

Figure 1:
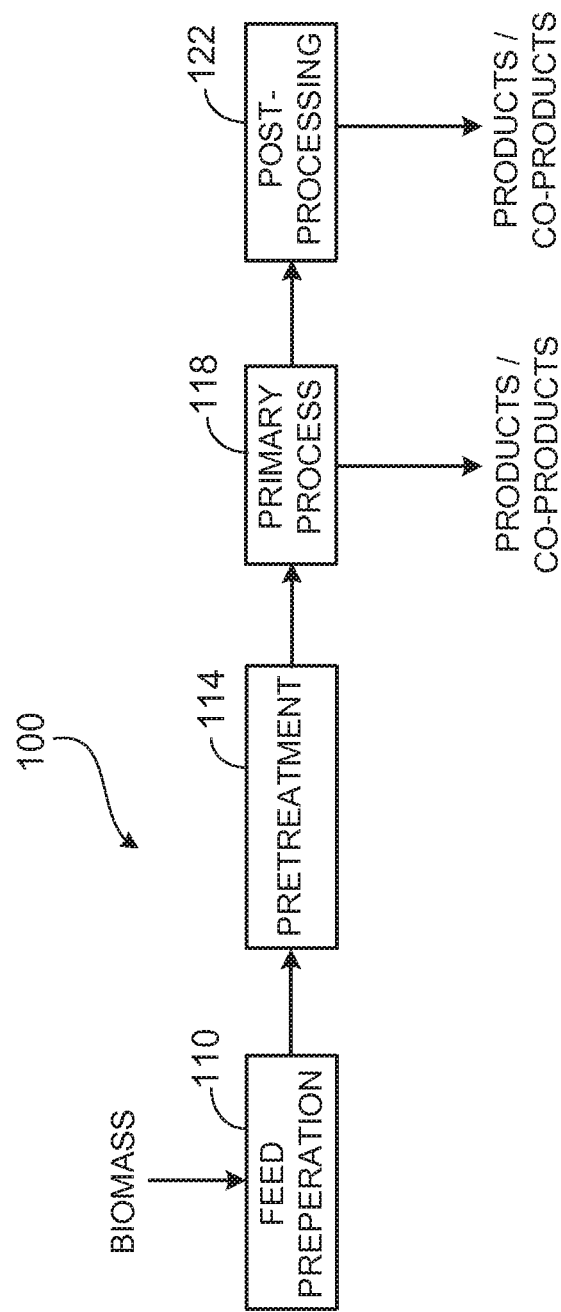
FIG. 1 is a block diagram illustrating conversion of biomass into products and co-products.

Treating biomass with radiation is useful for producing fuel and products. Generally biomass material is physically prepared before treatment with radiation. The material can be prepared so as to render it more uniform, e.g., to reduce particle size, to alter water content, to control viscosity, and so forth. The material is treated with radiation to alter the molecular and/or supra-molecular structure. In addition, the material can be treated in other ways, for example, with sonication, oxidation, pyrolysis, and steam explosion. The resulting material can be stored or used in a variety ways.

One application is fermentation to produce a combustible product, such as an alcohol. Microorganisms can be combined with the resulting material, and, optionally, other ingredients. The combination is fermented and product is recovered. For example, alcohols can be recovered by distillation.

In some embodiments, the radiation is applied on a large scale, for example to a batch of at least 50 kg, 100 kg, or 500 kg. The treatment can also be applied in a continuous or semi-continuous mode, for example, to material that moves under a radiation beam, e.g., so as to process at least 100, 500, 1000, 5000, or 20000 kg per hour.

A variety of biomass materials can be used as a starting material. Examples of biomass include plant biomass, animal biomass, and municipal waste biomass. Biomass also includes feedstock materials such as cellulosic and/or lignocellulosic materials.

Often biomass is material that includes a carbohydrate, such as cellulose. Generally, any biomass material that is or includes carbohydrates composed entirely of one or more saccharide units or that include one or more saccharide units can be processed by any of the methods described herein. For example, the biomass material can be cellulosic or lignocellulosic materials, or starchy materials, such as kernels of corn, grains of rice or other foods.

Additional examples of biomass materials include paper, paper products, wood, wood-related materials, particle board, grasses, rice hulls, bagasse, cotton, jute, hemp, flax, bamboo, sisal, abaca, straw, corn cobs, rice hulls, coconut hair, algae, seaweed, cotton, synthetic celluloses, or mixtures of any of these. Still other examples are described in WO 2008/073186, filed Oct. 26, 2007, and U.S. Ser. No. 12/429,045, filed Apr. 23, 2009.

Various biomass materials are often readily available, but—unless pretreated—can sometimes be difficult to process, e.g., by fermentation, or can give sub-optimal yields at a slow rate. In the methods described herein, feedstock materials can be first physically prepared for processing, often by size reduction of raw feedstock materials. Physically prepared feedstock can be pretreated or processed using one or more of radiation, sonication, oxidation, pyrolysis, and steam explosion. The various pretreatment systems and methods can be used in combinations of two, three, or even four of these technologies. Combinations of various pretreatment methods are generally disclosed in WO 2008/073186, for example.

In some cases, to provide materials that include a carbohydrate, such as cellulose, that can be converted by a microorganism to a number of desirable products, such as a combustible fuels (e.g., ethanol, butanol or hydrogen), feedstocks that include one or more saccharide units can be treated by any one or more of multiple processes. Other products and co-products that can be produced include, for example, human food, animal feed, pharmaceuticals, and nutriceuticals. Examples of other products are described in U.S. Ser. Nos. 12/417,900, 12/417,707, 12/417,720, and 12/417,731, all of which were filed Apr. 3, 2009.

Where the biomass is or includes a carbohydrate it may include, for example, a material having one or more $\beta$-1,4-linkages and having a number average molecular weight between about 3,000 and 50,000. Such a carbohydrate is or includes cellulose (I), which is derived from ($\beta$-glucose 1) through condensation of $\beta(1\rightarrow 4)$-glycosidic bonds. This linkage contrasts itself with that for $\alpha(1\rightarrow 4)$-glycosidic bonds present in starch and other carbohydrates.

Starchy materials include starch itself, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, oca, sago, sorghum, regular household potatoes, sweet potato, taro, yams, or one or more beans, such as favas, lentils or peas. Blends of any one or more starchy material are also starchy materials. In particular embodiments, the starchy material is derived from corn. Various corn starches and derivatives are described in "Corn Starch," Corn Refiners Association (11th Edition, 2006).

Biomass materials that include low molecular weight sugars can, e.g., include at least about 0.5 percent by weight of the low molecular sugar, e.g., at least about 2, 3, 4, 5, 6, 7, 8, 9, 10, 12.5, 25, 35, 50, 60, 70, 80, 90 or even at least about 95 percent by weight of the low molecular weight sugar. In some instances, the biomass is composed substantially of the low molecular weight sugar, e.g., greater than 95 percent by weight, such as 96, 97, 98, 99 or substantially 100 percent by weight of the low molecular weight sugar.

Biomass materials that include low molecular weight sugars can be agricultural products or food products, such as sugarcane and sugar beets or an extract therefrom, e.g., juice from sugarcane, or juice from sugar beets. Biomass materials that include low molecular weight sugars can be substantially pure extracts, such as raw or crystallized table sugar (sucrose). Low molecular weight sugars include sugar derivatives. For example, the low molecular weight sugars can be oligomeric (e.g., equal to or greater than a 4-mer, 5-mer, 6-mer, 7-mer, 8-mer, 9-mer or 10-mer), trimeric, dimeric, or monomeric. When the carbohydrates are formed of more than a single repeat unit, each repeat unit can be the same or different.

Specific examples of low molecular weight sugars include cellobiose, lactose, sucrose, glucose and xylose, along with derivatives thereof. In some instances, sugar derivatives are more rapidly dissolved in solution or utilized by microbes to provide a useful material, such as ethanol or butanol.

Combinations of any biomass materials described herein (e.g., combinations of any biomass materials, components, products, and/or co-products generated using the methods described herein) can be utilized for making any of the products described herein, such as ethanol. For example, blends of cellulosic materials and starchy materials can be utilized for making products.

Fuels and other products (e.g., ethanol, bioethanol, other alcohols, and other combustible hydrocarbons) produced via the methods disclosed herein can be blended with other hydrocarbon-containing species. For example, ethanol produced using any of the methods disclosed herein can be blended with gasoline to produce "gasohol," which can be used as combustible fuel in a wide variety of applications, including automobile engines.

Biomass Treatment Processes

FIG. 1 shows a for converting biomass, particularly biomass with significant cellulosic and lignocellulosic components and/or starchy components, into useful products and co-products. System 100 includes a feed preparation subsystem 110, a pretreatment subsystem 114, a primary process subsystem 118, and a post-processing subsystem 122. Feed preparation subsystem 110 receives biomass in its raw form, physically prepares the biomass for use as feedstock by downstream processes (e.g., reduces the size of and homogenizes the biomass), and stores the biomass both in its raw and feedstock forms.

Biomass with significant cellulosic and/or lignocellulosic components, or starchy components can have a high average molecular weight and crystallinity that be modified by one or more pretreatments to facilitate use of the material.

Pretreatment subsystem 114 receives feedstock from the feed preparation subsystem 110 and prepares the feedstock for use in primary production processes by, for example, reducing the average molecular weight and crystallinity of the feedstock and/or increasing the surface area and/or porosity of the feedstock. In some cases, the pre-treated biomass material has a low moisture content, e.g., less than about 7.5, 5, 3, 2.5, 2, 1.5, 1, or 0.5 percent water by weight. Moisture reduction can be achieved, e.g., by drying biomass material. Pretreatment processes can avoid the use of harsh chemicals such as strong acids and bases.

Primary process subsystem 118 receives pretreated feedstock from pretreatment subsystem 114 and produces useful products (e.g., ethanol, other alcohols, pharmaceuticals, and/or food products). Primary production processes typically include processes such as fermentation (e.g., using microorganisms such as yeast and/or bacteria), chemical treatment (e.g., hydrolysis), and gasification.

In some cases, the output of primary process subsystem 118 is directly useful but, in other cases, the output requires further processing provided by post-processing subsystem 122. Post-processing subsystem 122 provides further processing to product streams from primary process system 118 (e.g., distillation and denaturation of ethanol) as well as treatment for waste streams from the other subsystems. In some cases, the co-products of subsystems 114, 118, 122 can also be directly or indirectly useful as secondary products and/or in increasing the overall efficiency of system 100. For example, post-processing subsystem 122 can produce treated water to be recycled for use as process water in other subsystems and/or can produce burnable waste which can be used as fuel for boilers producing steam and/or electricity. In general, post-processing steps can include one or more steps such as distillation to separate different components, wastewater treatment (e.g., screening, organic equalization, sludge conversion), mechanical separation, and/or waste combustion.

Ion Beam Systems for Biomass Pretreatment

Ion beam pretreatment (e.g., exposure to ions) of biomass can be a particularly efficient, economical, and high-throughput treatment method. Ion beam pretreatment generally includes exposing biomass (mechanically processed, or unprocessed) to one or more different types of ions generated in one or more ion sources. The ions can be accelerated in accelerator systems that are coupled to the ion sources, and can produce ions with varying energies and velocities. Typically, in ion-based pretreatment, ions are not accelerated to sufficient energies to cause large amounts of x-ray radiation to be produced. Accordingly, vaulting and shielding requirements for ion sources can be considerably relaxed relative to similar requirements for electron sources.

When ion beam radiation is utilized, it can be applied to any sample that is dry or wet, or even dispersed in a liquid, such as water. For example, ion beam irradiation can be performed on cellulosic and/or lignocellulosic material in which less than about 25 percent by weight of the cellulosic and/or lignocellulosic material has surfaces wetted with a liquid, such as water. In some embodiments, ion beam irradiating is performed on cellulosic and/or lignocellulosic material in which substantially none of the cellulosic and/or lignocellulosic material is wetted with a liquid, such as water.

When ion beam irradiation is utilized, it can be applied while the cellulosic and/or lignocellulosic material is exposed to air, oxygen-enriched air, or even oxygen itself, or blanketed by an inert gas such as nitrogen, argon, or helium. When oxidation of the biomass material is desired, an oxidizing environment is utilized, such as air or oxygen, and the properties of the ion beam source can be adjusted to induce reactive gas formation, e.g., formation of ozone and/or oxides of nitrogen. These reactive gases react with the biomass material, alone or together with incident ions, to cause degradation of the material. As an example, when ion beam exposure of biomass is utilized, the biomass can be exposed to ions under a pressure of one or more gases of greater than about 2.5 atmospheres, such as greater than 5, 10, 15, 20 or even greater than about 50 atmospheres.

Ions that are incident on biomass material typically scatter from and ionize portions of the biomass via Coulomb scattering. The interaction between the ions and the biomass can also produce energetic electrons (e.g., secondary electrons) that can further interact with the biomass (e.g., causing further ionization). Ions can be positively charged or negatively charged, and can bear a single positive or negative charge, or multiple charges, e.g., one, two, three or even four or more charges. In instances in which chain scission is desired, positively charged particles may be desirable, in part, due to their acidic nature.

The ions to which biomass material is exposed can have the mass of a resting electron, or greater, e.g., 500, 1000, 1500, or 2000 or more, e.g., 10,000 or even 100,000 times the mass of a resting electron. For example, the ions can have a mass of from about 1 atomic unit to about 150 atomic units, e.g., from about 1 atomic unit to about 50 atomic units, or from about 1 to about 25, e.g., 1, 2, 3, 4, 5, 10, 12 or 15 amu. Exemplary ions and ion accelerators are discussed in Introductory Nuclear Physics, Kenneth S. Krane, John Wiley & Sons, Inc. (1988), Krsto Prelec, FIZIKA B 6 (1997) 4, 177-206, Chu, William T., "Overview of Light-Ion Beam Therapy", Columbus-Ohio, ICRU-IAEA Meeting, 18-20 Mar. 2006, Iwata, Y. et al., "Alternating-Phase-Focused IH-DTL for Heavy-Ion Medical Accelerators", Proceedings of EPAC 2006, Edinburgh, Scotland, and Leitner, C. M. et al., "Status of the Superconducting ECR Ion Source Venus", Proceedings of EPAC 2000, Vienna, Austria.

A wide variety of different types of ions can be used to pretreat biomass material. For example, protons, helium nuclei, argon ions, silicon ions, neon ions, carbon ions, phosphorus ions, oxygen ions or nitrogen ions can be utilized. In some embodiments, the ions can induce higher amounts of chain scission than an equivalent dose of electrons. In some instances, positively charged ions can induce higher amounts of chain scission and/or other processes than negatively charged ions due to their acidity. Alternatively, in certain embodiments, depending upon the nature of the biomass, negatively charged ions can be more effective than positively charged ions at inducing chain scission and/or other processes, due to their alkaline nature.

Following generation and/or acceleration, the average energy of ions in an ion beam can be from about 1.0 MeV/atomic unit to about 6,000 MeV/atomic unit, e.g., from about 3 MeV/atomic unit to about 4,800 MeV/atomic unit, or from about 10 MeV/atomic unit to about 1,000 MeV/atomic unit.

In general, many different types of ions can be used to irradiate biomass materials. For example, in some embodiments, ion beams can include relatively light ions, such as protons and/or helium ions. In certain embodiments, the ion beams can include moderately heavier ions, such as carbon ions, nitrogen ions, oxygen ions, and/or neon ions. In some embodiments, ion beams can include still heavier ions, such as argon ions, silicon ions, phosphorus ions, sodium ions, calcium ions, and/or iron ions.

In certain embodiments, ion beams used to irradiate biomass materials can include more than one different type of ion. For example, ion beams can include mixtures of two or more (e.g., three, four, five, six or more) different types of ions. Exemplary mixtures can include carbon ions and protons, carbon ions and oxygen ions, nitrogen ions and protons, and iron ions and protons. More generally, mixtures of any of the ions discussed herein (or any other ions) can be used to form ion beams that are used to irradiate biomass. In particular, mixtures of relatively light and relatively heavier ions can be used in a single ion beam, where each of the different types of ions has different effectiveness in irradiating different types of biomass materials.

In some embodiments, ion beams for irradiating biomass materials include positively-charged ions. The positively charged ions can include, for example, positively charged hydrogen ions (e.g., protons), noble gas ions (e.g., helium, neon, argon), carbon ions, nitrogen ions, oxygen ions, silicon atoms, phosphorus ions, and metal ions such as sodium ions, calcium ions, and/or iron ions. Without wishing to be bound by any theory, it is believed that such positively-charged ions behave chemically as Lewis acid moieties when exposed to biomass materials, initiating and sustaining reactions such as cationic ring- and chain-opening scission reactions in an acidic and/or oxidative environment.

In certain embodiments, ion beams for irradiating biomass materials include negatively-charged ions. Negatively charged ions can include, for example, negatively charged hydrogen ions (e.g., hydride ions), and negatively charged ions of various relatively electronegative nuclei (e.g., oxygen ions, nitrogen ions, carbon ions, silicon ions, and phosphorus ions). Without wishing to be bound by any theory, it is believed that such negatively-charged ions behave chemically as Lewis base moieties when exposed to biomass materials, causing anionic ring- and chain-opening scission reactions in a basic and/or reducing environment.

In some embodiments, beams for irradiating biomass materials can include neutral atoms. For example, any one or more of hydrogen atoms, helium atoms, carbon atoms, nitrogen atoms, oxygen atoms, neon atoms, silicon atoms, phosphorus atoms, argon atoms, and iron atoms can be included in beams that are used for irradiation of biomass materials. In general, mixtures of any two or more of the above types of atoms (e.g., three or more, four or more, or even more) can be present in the beams.

The preceding discussion has focused on ion beams that include mononuclear ions and/or neutral particles (e.g., atomic ions and neutral atoms). Typically, such particles are the easiest—in energetic terms—to generate, and parent particles from which these species are generated may be available in abundant supply. However, in some embodiments, beams for irradiating biomass materials can include one or more types of ions or neutral particles that are polynuclear, e.g., including multiple nuclei, and even including two or more different types of nuclei. For example, ion beams can include positive and/or negative ions and/or neutral particles formed from species such as $N_2$, $O_2$, $H_2$, $CH_4$, and other molecular species. Ion beams can also include ions and/or neutral particles formed from heavier species that include even more nuclei, such as various hydrocarbon-based species and/or various inorganic species, including coordination compounds of various metals.

In certain embodiments, ion beams used to irradiate biomass materials include singly-charged ions such as one or more of $H^+$, $H^-$, $He^+$, $Ne^+$, $Ar^+$, $C^+$, $C^-$, $O^+$, $O^-$, $N^+$, $N^-$, $Si^+$, $Si^-$, $P^+$, $P^-$, $Na^+$, $Ca^+$, $Fe^+$, $Rh^+$, $Ir^+$, $Pt^+$, $Re^+$, $Ru^+$, and $Os^+$. In some embodiments, ion beams can include multiply-charged ions such as one or more of $C^{2+}$, $C^{3+}$, $C^{4+}$, $N^{3+}$, $N^{5+}$, $N^{3-}$, $O^{2+}$, $O^{2-}$, $O_2^{2-}$, $Si^{2+}$, $Si^{4+}$, $Si^{2-}$, and $Si^{4-}$. In general, the ion beams can also include more complex polynuclear ions that bear multiple positive or negative charges. In certain embodiments, by virtue of the structure of the polynuclear ion, the positive or negative charges can be effectively distributed over substantially the entire structure of the ion. In some embodiments, the positive or negative charges can be somewhat localized over portions of the structure of the ions, by virtue of the electronic structures of the ions. Generally, ion beams used to irradiate biomass materials can include ions—both positive and/or negative—of any of the molecular species disclosed herein, and the ions can generally include one or multiple charges. The ion beams can also include other types of ions, positively and/or negatively charged, bearing one or multiple charges.

Ions and ion beams can be generated using a wide variety of methods. For example, hydrogen ions (e.g., both protons and hydride ions) can be generated by field ionization of hydrogen gas and/or via thermal heating of hydrogen gas. Noble gas ions can be generated by field ionization. Ions of carbon, oxygen, and nitrogen can be generated by field ionization, and can be separated from one another (when they are co-generated) by a hemispherical analyzer. Heavier ions such as sodium and iron can be produced via thermionic emission from a suitable target material. Suitable methods for generating ion beams are disclosed, for example, in U.S. Provisional Application Nos. 61/049,406 and 61/073,665, and in U.S. Ser. No. 12/417,699.

A wide variety of different particle beam accelerators can be used to accelerate ions prior to exposing biomass material to the ions. For example, suitable particle beam accelerators include Dynamitron® accelerators, Rhodotron® accelerators, static accelerators, dynamic linear accelerators (e.g., LINACs), van de Graaff accelerators, and folded tandem Pelletron accelerators. These and other suitable accelerators are discussed, for example, in U.S. Provisional Application Nos. 61/049,406 and 61/073,665, and in U.S. Ser. No. 12/417,699.

In some embodiments, combinations of two or more of the various types of accelerators can be used to produce ion beams that are suitable for treating biomass. For example, a folded tandem accelerator can be used in combination with a linear accelerator, a Rhodotron® accelerator, a Dynamitron® accelerator, a static accelerator, or any other type of accelerator to produce ion beams. Accelerators can be used in series, with the output ion beam from one type of accelerator directed to enter another type of accelerator for additional acceleration. Alternatively, multiple accelerators can be used in parallel to generate multiple ion beams for biomass treatment. In certain embodiments, multiple accelerators of the same type can be used in parallel and/or in series to generate accelerated ion beams.

In some embodiments, multiple similar and/or different accelerators can be used to generate ion beams having different compositions. For example, a first accelerator can be used to generate one type of ion beam, while a second accelerator can be used to generate a second type of ion beam. The two ion beams can then each be further accelerated in another accelerator, or can be used to treat biomass.

Further, in certain embodiments, a single accelerator can be used to generate multiple ion beams for treating biomass. For example, any of the accelerators discussed herein (and other types of accelerators as well) can be modified to produce multiple output ion beams by sub-dividing an initial ion current introduced into the accelerator from an ion source. Alternatively, or in addition, any ion beam produced by any of the accelerators disclosed herein can include only a single type of ion, or multiple different types of ions.

In general, where multiple different accelerators are used to produce one or more ion beams for treatment of biomass, the multiple different accelerators can be positioned in any order with respect to one another. This provides for great flexibility in producing one or more ion beams, each of which has carefully selected properties for treating biomass (e.g., for treating different components in biomass).

The ion accelerators disclosed herein can also be used in combination with any of the other biomass treatment steps. For example, in some embodiments, electrons and ions can be used in combination to treat biomass. The electrons and ions can be produced and/or accelerated separately, and used to treat biomass sequentially (in any order) and/or simultaneously. In certain embodiments, electron and ion beams can be produced in a common accelerator and used to treat biomass. Certain ion accelerators can be configured to produce electron beams as an alternative to, or in addition to, ion beams. For example, Dynamitron® accelerators, Rhodotron® accelerators, and LINACs can be configured to produce electron beams for treatment of biomass.

Moreover, pretreatment of biomass with ion beams can be combined with other biomass pretreatment methods such as sonication, pyrolysis, oxidation, steam explosion, and/or irradiation with other forms of radiation (e.g., electrons, gamma radiation, x-rays, ultraviolet radiation). In general, other pretreatment methods such as sonication-based pretreatment can occur before, during, or after ion-based biomass pretreatment.

Exposure Conditions and Ion Beam Properties

In general, when a condensed medium is exposed to a charged particle beam, the charged particles penetrate the medium and deposit within the medium at a distribution of depths below the surface upon which the particles are incident. It has generally been observed (see, for example, FIG. 1 in Prelec (infra, 1997)) that the dose distribution for ions includes a significantly sharper maximum (the Bragg peak), and that ions exhibit significantly less lateral scattering, than other particles such as electrons and neutrons and other forms of electromagnetic radiation such as x-rays. Accordingly, due to the relatively well-controlled dosing profile of accelerated ions, they operate relatively efficiently to alter the structure of biomass material. Furthermore, as is apparent from FIG. 6 of Prelec (infra, 1997), heavier ions (such as carbon ions) have even sharper dosing profiles than lighter ions such as protons, and so the relative effectiveness of these heavier ions at treating biomass material is even greater than for lighter ions.

In some embodiments, the average energy of the accelerated ions that are incident on biomass material is 1 MeV/u or more (e.g., 2, 3, 4, 5, 6, 7, 8, 9, 10, 12, 15, 20, 30, 50, 100, 300, 500, 600, 800, or even 1000 MeV/u or more).

In certain embodiments, the average energy of the accelerated ions is 10 MeV or more (e.g., 20, 30, 50, 100, 200, 300, 400, 500, 600, 800, 1000, 2000, 3000, 4000, or even 5000 MeV or more).

In certain embodiments, an average velocity of the accelerated ions is 0.0005 c or more (e.g., 0.005 c or more, 0.05 c or more, 0.1 c or more, 0.2 c or more, 0.3 c or more, 0.4 c or more, 0.5 c or more, 0.6 c or more, 0.7 c or more, 0.8 c or more, 0.9 c or more), where c represents the vacuum velocity of light. In general, for a given accelerating potential, lighter ions are accelerated to higher velocities than heavier ions. For example, for a given accelerating potential, a maximum velocity of a hydrogen ion may be about 0.05 c, while a maximum velocity of a carbon ion may be about 0.0005 c. These values are only exemplary; the velocity of the accelerated ions depends on the accelerating potential applied, the mode of operation of the accelerator, the number of passes through the accelerating field, and other such parameters.

In some embodiments, an average ion current of the accelerated ions is $10^5$ particles/s or more (e.g., $10^6$, $10^7$, $10^8$, $10^9$, $10^{10}$, $10^{11}$, $10^{12}$, $10^{13}$, $10^{14}$, $10^{15}$, or even $10^{16}$ particles/s or more).

In some embodiments, a radiation dose delivered to biomass material from an ion beam is 5 Mrad or more (e.g., 10, 15, 20, 30, 40, 50, 60, 80, or even 100 Mrad or more).

Figure 2:
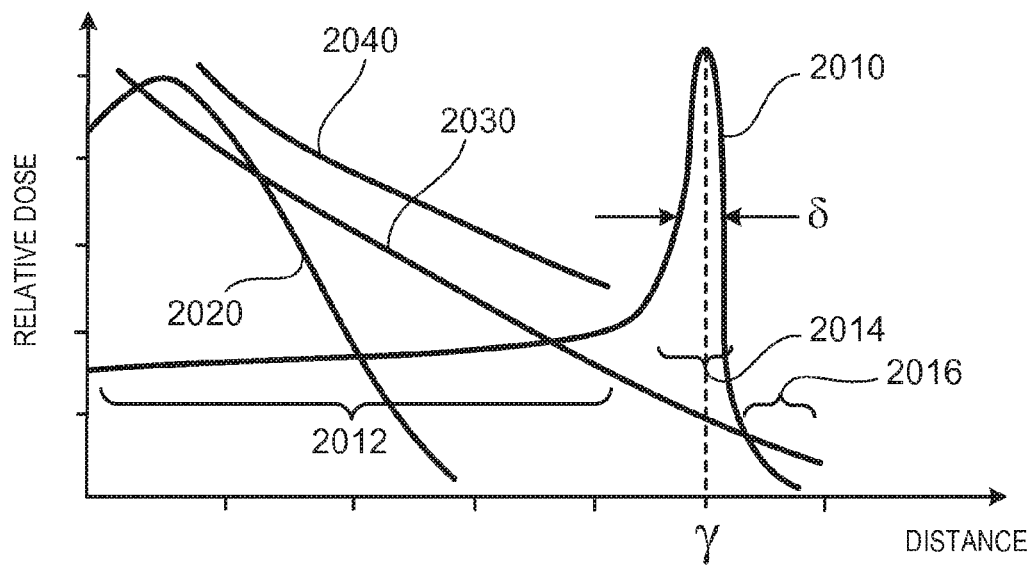
FIG. 2 is a schematic diagram showing dose profiles for ions, electrons, and photons in a condensed-phase material.

When a sample is exposed to an ion beam, energy is deposited in the sample according to an ion dose profile (also sometimes referred to as a depth-dose distribution). FIG. 2 shows a schematic diagram of a representative ion dose profile 2010 for a condensed-phase biomass sample. The vertical axis of ion dose profile 2010 in FIG. 2 shows the relative ion dose, plotted as a function of depth below a surface of the sample that is exposed to the ion beam, on the horizontal axis. FIG. 2 also includes, for comparative purposes, an electron dose profile 2020, a gamma radiation dose profile 2030, and an x-ray dose profile 2040.

As shown in FIG. 2, both gamma radiation and x-ray radiation (and further, other types of electromagnetic radiation) are absorbed strongly in a region adjacent to the surface of the sample, leading to the highest energy doses being deposited near the sample surface. Gamma and x-ray radiation dose profiles 2030 and 2040 decrease approximately exponentially from the surface of the sample, as progressively fewer photons are able to penetrate deeper into the sample to be absorbed.

Electron dose profile 2020 shows a build-up effect whereby, due to the penetrating ability of Compton electrons, the deposited energy dose increases in the vicinity of the exposed surface of the sample to a maximum deposited dose at a penetration depth of, typically, about 3-4 cm in condensed media. Thereafter, the relative dose of deposited energy decreases relatively rapidly with increasing distance beneath the sample surface.

Ion beams, in contrast, typically have dose profiles that are sometimes described as being inverse with respect to the dose profiles of electrons and photons. As shown in FIG. 2, ion dose profile 2010 includes a region 2012 in which a relatively constant energy dose is applied to the sample. Thereafter, ion dose profile 2010 includes a region 2014 referred to as the Bragg peak, which corresponds to a portion of the sample into which a comparatively larger fraction of the ion beam's energy is deposited, followed by a region 2016 in which a much smaller energy dose is deposited. The Bragg peak, which has a full width at half maximum (FWHM) of $\delta$, ensures that the dose profile for ions differs significantly from the dose profiles for electrons and photons of various wavelengths. As a result, exposing materials such as biomass materials to ion beams can yield effects that are different from the effects produced by photons and electron beams.

Typically, the width $\delta$ of Bragg peak 2014 depends upon a number of factors, including the nature of the sample, the type of ions, and the average ion energy. One important factor that influences the width $\delta$ of Bragg peak 2014 is the distribution of energies in the incident ion beam. In general, the narrower the distribution of energies in the incident ion beam, the narrower the width $\delta$ of Bragg peak 2014. As an example, Bragg peak 2014 typically has a width of about 3 mm or less for a distribution of ion energies that has a FWHM of 1 keV or less. The width $\delta$ of Bragg peak 2014 can be much less than 3 mm under these conditions as well, e.g., 2.5 mm or less, 2.0 mm or less, 1.5 mm or less, 1.0 mm or less.

The position of Bragg peak 2014, indicated by $\gamma$ in FIG. 2, depends upon a number of factors including the average energy of the incident ion beam. In general, for larger average ion beam energies, Bragg peak 2014 will shift to larger depths in FIG. 2, because higher-energy ions have the ability to penetrate more deeply into a material before most of the ions' kinetic energy is lost via scattering events.

Figure 3:
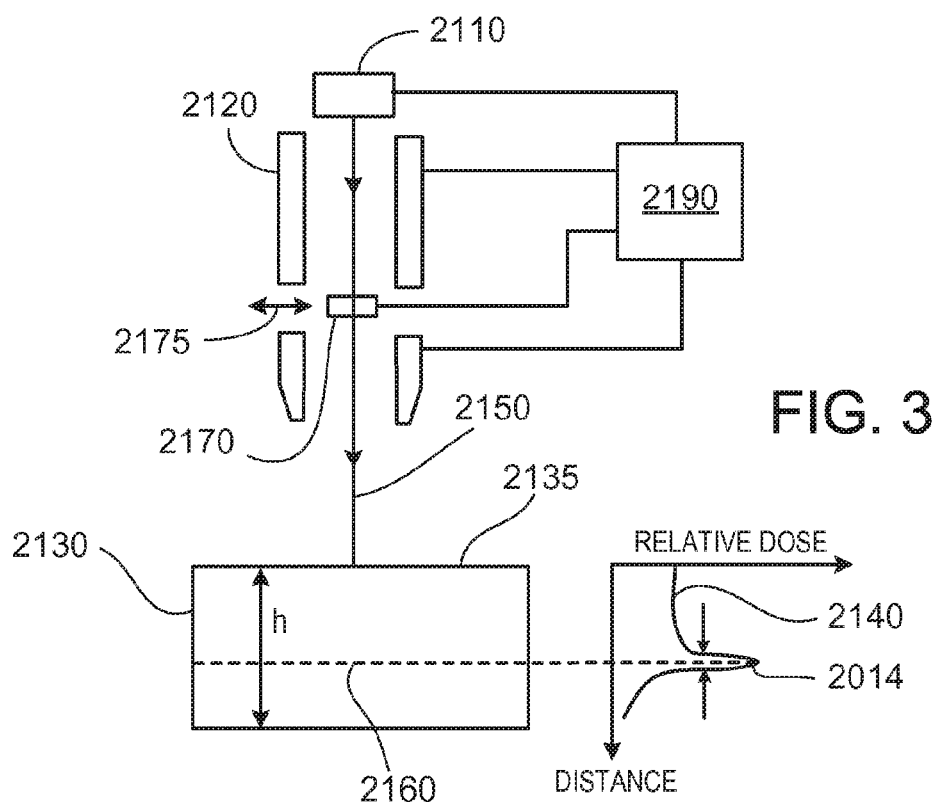
FIG. 3 is a schematic diagram of an ion beam exposure system.

Various properties of one or more incident ion beams can be adjusted to expose samples (e.g., biomass materials) to ion beam radiation, which can lead to de-polymerization and other chain-scission reactions in the samples, reducing the molecular weight of the samples in a predictable and controlled manner. FIG. 3 shows a schematic diagram of an ion beam exposure system 2100. System 2100 includes an ion source 2110 that generates an ion beam 2150. Optical elements 2120 (including, for example, lenses, apertures, deflectors, and/or other electrostatic and/or magnetic elements for adjusting ion beam 2150) direct ion beam 2150 to be incident on sample 2130, which has a thickness h in a direction normal to surface 2135 of sample 2130. In addition to directing ion beam 2150, optical elements 2120 can be used to control various properties of ion beam 2150, including collimation and focusing of ion beam 2150. Sample 2130 typically includes, for example, one or more of the various types of biomass materials that are discussed herein. System 2100 also includes an electronic controller 2190 in electrical communication with the various components of the system (and with other components not shown in FIG. 3). Electronic controller 2190 can control and/or adjust any of the system parameters disclosed herein, either fully automatically or in response to input from a human operator.

FIG. 3 also shows the ion dose profile that results from exposure of sample 2130 to ion beam 2150. The position 2160 of the Bragg peak within sample 2130 depends upon the average energy of ion beam 2150, the nature of the ions in ion beam 2150, the material from which sample 2130 is formed, and other factors.

In many applications of ion beams, such as ion therapy for tumor eradication, the relatively small width $\delta$ of Bragg peak 2014 is advantageous, because it allows reasonably fine targeting of particular tissues within a patient undergoing therapy, and helps to reduce damage due to exposure of nearby benign tissues.

However, when exposing biomass materials such as sample 2130 to ion beam 2150, the relatively small width $\delta$ of Bragg peak 2014 can restrict throughput. Typically, for example, the thickness h of sample 2130 is larger than the width $\delta$ of Bragg peak 2014. In some embodiments, h can be substantially larger than $\delta$ (e.g., larger by a factor of 5 or more, or 10 or more, or 20 or more, or 50 or more, or 100 or more, or even more).

To increase a thickness of sample 2130 in which a selected dose can be delivered in a particular time interval, the energy distribution of ion beam 2150 can be adjusted. Various methods can be used to adjust the energy distribution of ion beam 2150. One such method is to employ one or more removable scattering elements 2170 positioned in the path of ion beam 2150, as shown in FIG. 3. Scattering element 2170 can be, for example, a thin membrane formed of a metal material such as tungsten, tantalum, copper, and/or a polymer-based material such as Lucite® polymer.

Figure 4A:
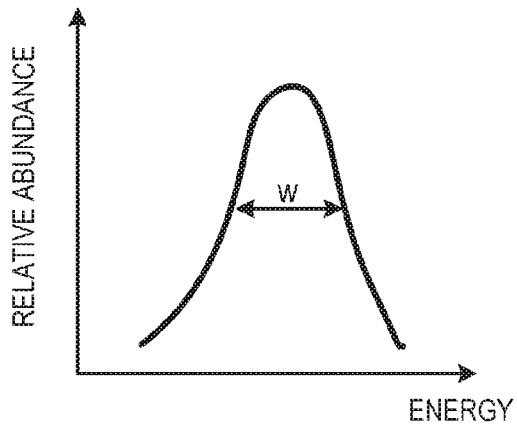
FIGS. 4A and 4B are schematic diagrams showing ion beam energy distributions.
Figure 4B:
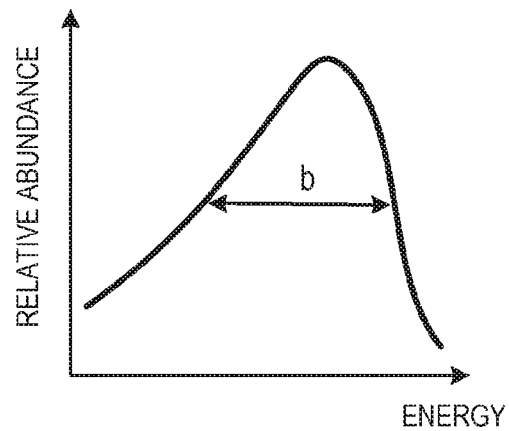

Prior to passing through scattering element 2170, ion beam 2150 has an energy distribution of width w, shown in FIG. 4A. When ion beam 2150 passes through element(s) 2170, at least some of the ions in ion beam 2150 undergo scattering events with atoms in element(s) 2170 transferring a portion of their kinetic energy to the atoms of element(s) 2170. As a result, the energy distribution of ion beam 2150 is broadened to a width b larger than w, as shown in FIG. 4B. In particular, the energy distribution of ion beam 2150 acquires a broader low-energy tail as a result of scattering in element(s) 2170.

Figure 4C:
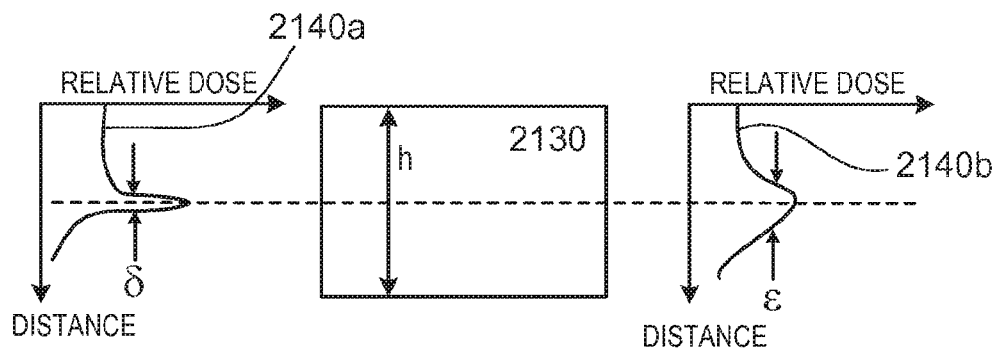
FIG. 4C is a schematic diagram showing ion dose profiles in an exposed sample.

FIG. 4C shows the effect of broadening the ion energy distribution of ion beam 2150 on the ion dose profiles in sample 2130. Ion dose profile 2140a is produced by exposing sample 2130 to ion beam 2150 having the ion energy distribution shown in FIG. 4A. Ion dose profile 2140a includes a relatively narrow Bragg peak. As a result, the region of sample 2130 in which a relatively high dose is deposited is small. In contrast, by broadening the ion energy distribution of ion beam 2150 to yield the distribution shown in FIG. 4B, ion dose profile 2140b is obtained in sample 2130 after exposing the sample to the broadened distribution of ion energies. As dose profile 2140b shows, by broadening the ion energy distribution, the region of sample 2130 in which a relatively high dose is deposited is increased relative to ion dose profile 2140a. By increasing the region of sample 2130 exposed to a relatively high dose, the throughput of the exposure process can be improved.

In certain embodiments, the width b of the broadened energy distribution can be larger than w by a factor of 1.1 or more (e.g., 1.2, 1.3, 1.4, 1.5, 1.7, 2.0, 2.5, 3.0, 3.5, 4.0, 5.0, or even 10.0 or more).

Typically, the ion dose profile in sample 2130 produced by exposure of the sample to the broadened ion energy distribution shown in FIG. 4B has a Bragg peak having a full width at half maximum (FWHM) of $\epsilon$. As a result of broadening the ion energy distribution, $\epsilon$ can be larger than $\delta$ by a factor of 1.1 or more (e.g., 1.2 or more, 1.3 or more, 1.5 or more, 1.7 or more, 2.0 or more, 2.5 or more, 3.0 or more, 4.0 or more, 5.0 or more, 6.0 or more, 7.0 or more, 10.0 or more).

For sample 2130 of thickness h, after broadening the ion energy distribution of ion beam 2150 and exposing the sample to the ion beam, a ratio of $\epsilon/h$ can be $1\times10^{-6}$ or more (e.g., $1\times10^{-5}$, $5\times10^{-5}$, $1\times10^{-4}$, $5\times10^{-4}$, $1\times10^{-3}$, $5\times10^{-3}$, 0.01, 0.05, 0.08, 0.1, or even 0.5 or more).

In certain embodiments, sample 2130 includes a plurality of particles (e.g., approximately spherical particles, and/or fibers, and/or filaments, and/or other particle types). In general, the particles have a distribution of different sizes, with an average particle size r. The ion energy distribution of ion beam 2150 can be adjusted (e.g., via broadening) based on the average particle size r of sample 2130 to improve the efficiency of ion-based treatment of sample 2130. For example, ion beam 2150 can be adjusted so that a ratio of $\epsilon/r$ is 0.001 or more (e.g., 0.005 or more, 0.01 or more, 0.05 or more, 0.1 or more, 0.5 or more, 1.0 or more, 1.5 or more, 2.0 or more, 2.5 or more, 3.0 or more, 3.5 or more, 4.0 or more, 5.0 or more, 6.0 or more, 8.0 or more, 10 or more, 50 or more, 100 or more, 500 or more, 1000 or more, or even more).

Figure 5:
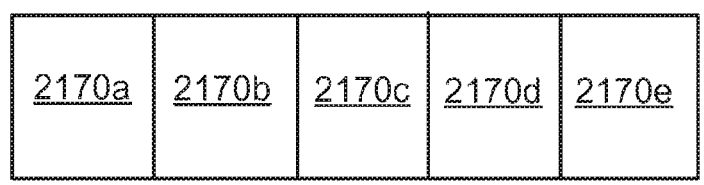
FIG. 5 is a schematic diagram of a scattering element that includes multiple sub-regions.

In some embodiments, a scattering element 2170 can include multiple different scattering sub-elements that are configured to broaden the distribution of ion energies in ion beam 2150 by different amounts. For example, FIG. 5 shows a multi-sub-element scattering element 2170 that includes sub-elements 2170a-e. Each of sub-elements 2170a-e broadens the distribution of ion energies in ion beam 2150 to a different extent. During operation of system 2100, electronic controller 2190 can be configured to select an appropriate sub-element of scattering element 2170 based on information such as the thickness h of sample 2130, the type of ions in ion beam 2150, and the average ion energy in ion beam 2150. The selection of an appropriate sub-element can be made in fully automated fashion, or based at least in part on input from a human operator. Selection of an appropriate sub-element is made by translating scattering element 2170 in the direction shown by arrow 2175 to position a selected sub-element in the path of ion beam 2150.

In certain embodiments, other devices can be used in addition to, or as an alternative to, scattering element(s) 2170. For example, in some embodiments, combinations of electric and or magnetic fields, produced by ion optical elements, can be used to broaden the ion energy distribution of ion beam 2150. Ion beam 2150 can pass through a first field configured to spatially disperse ions in the ion beam. Then the spatially dispersed ions can pass through a second field that is well-localized spatially, and which selectively retards only a portion of the spatially dispersed ions. The ions then pass through a third field that spatially re-assembles all of the ions into a collimated beam, which is then directed onto the surface of sample 2130. Typically, the ion optical elements used to generate the fields that adjust the ion energy distribution are controlled by electronic controller 2190. By applying spatially localized fields selectively, a high degree of control over the modified ion energy distribution is possible, including the generation of ion energy distributions having complicated profiles (e.g., multiple lobes). For example, in some embodiments, by applying a localized field that accelerates a portion of the spatially dispersed ion distribution, the ion energy distribution shown in FIG. 4A can be broadened on the high-energy side of the distribution maximum.

The information used by electronic controller 2190 to adjust the ion energy distribution of ion beam 2150 can include the thickness h of sample 2130, as discussed above. In some embodiments, electronic controller 2190 can use information about the expected ion dose profile in sample 2130 to adjust the ion energy distribution of ion beam 2150. Information about the expected ion dose profile can be obtained from a database, for example, that includes measurements of ion dose profiles acquired from literature sources and/or from calibration experiments performed on representative samples of the material from which sample 2130 is formed. Alternatively, or in addition, information about the expected ion dose profile can be determined from a mathematical model of ion interactions in sample 2130 (e.g., an ion scattering model).

In certain embodiments, the information about the expected ion dose profile can include information about the FWHM of the Bragg peak in the expected ion dose profile. The FWHM of the Bragg peak can be determined from measurements of ion dose profiles and/or from one or more mathematical models of ion scattering in the sample. Adjustments of the ion energy distribution of ion beam 2150 can be performed to reduce a difference between the thickness h of sample 2130 and the FWHM of the Bragg peak. In some embodiments, for example, a difference between h and the full width at half maximum of the Bragg peak is 20 cm or less (e.g., 18, 16, 14, 12, 10, 8, 6 cm, 5, 4, 3, 2, 1, 0.5, 0.1, 0.05, 0.01, 0.001, 0.0001, or even 0.00001 cm or less, or even zero).

Figure 6:
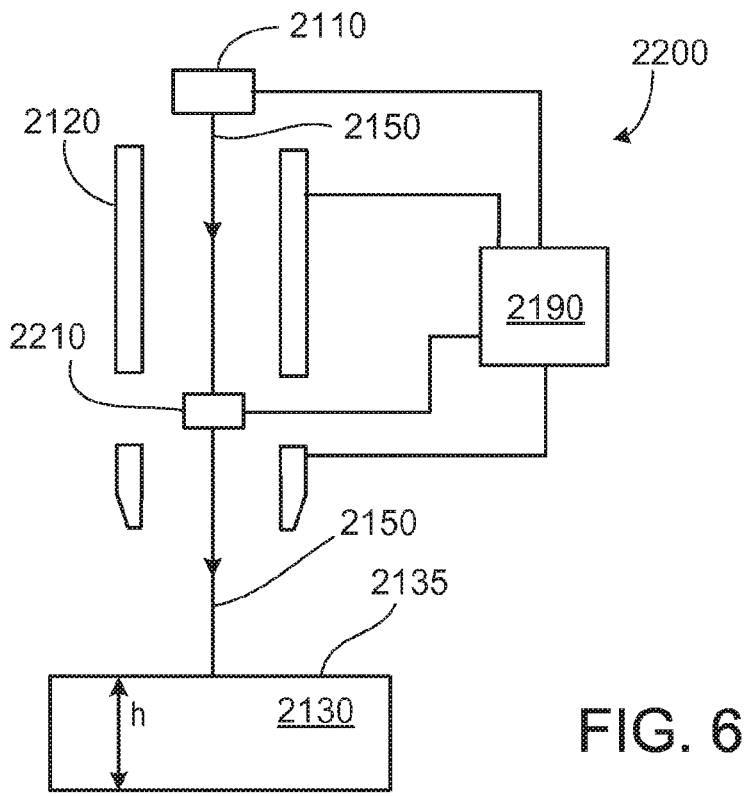
FIG. 6 is a schematic diagram of an ion beam exposure system that includes an ion filter.

In some embodiments, the ion beam exposure system can adjust the distribution of ion energies in ion beam 2150 in other ways. For example, the ion beam exposure system can be configured to filter the ion beam by removing ions from ion beam 2150 that have energies below a selected energy threshold and/or above a selected energy threshold. FIG. 6 shows an ion beam exposure system 2200 that includes an ion filter 2210 discussed in more detail below. The other components of system 2200 are similar to the components of system 2100, and will not be further discussed.

Figure 7A:
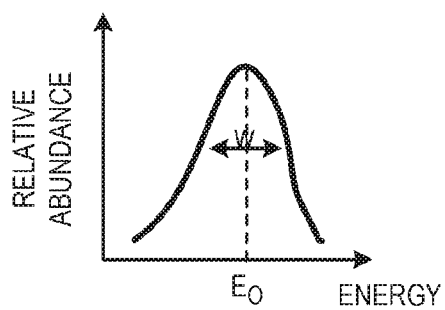
FIGS. 7A-C are schematic diagrams showing energy distributions for unfiltered and filtered ion beams.
Figure 7B:
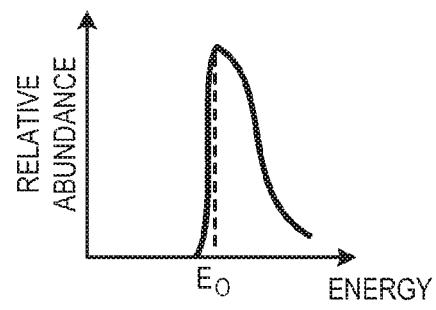

FIG. 7A shows an ion energy distribution corresponding to ion beam 2150 produced by ion source 2110. Ion beam 2150, with an energy distribution as shown in FIG. 7A, enters ion filter 2210 where the energy distribution of ion beam 2150 is adjusted by filtering out certain ions from the ion beam. For example, in some embodiments, ion filter 2210 can be configured to remove ions from ion beam 2150 that have an energy smaller than a selected energy threshold. In FIG. 7A, the selected energy threshold is the position $E_0$ of the peak in the ion energy distribution, although more generally, any energy threshold can be selected. By filtering out all (or even just a large fraction of) ions having an energy less than $E_0$, the ion energy distribution for ion beam 2150 is as shown in FIG. 7B.

Figure 7C:
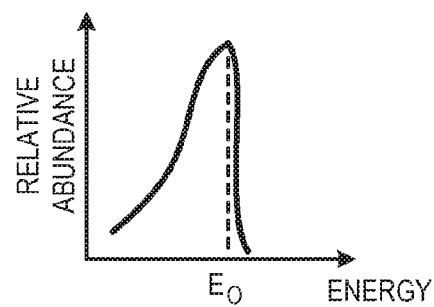

In contrast, in some embodiments, ion filter 2210 can be configured to remove ions from ion beam 2150 that have an energy larger than a selected energy threshold (when ion filter 2210 is implemented as a hemispherical analyzer, for example). For example, the selected energy threshold can correspond to the position $E_0$ of the peak in the ion energy distribution, although more generally, any energy threshold can be selected. By removing all (or even a large fraction of) ions from ion beam 2150 having an energy more than $E_0$, the ion energy distribution for ion beam 2150 is as shown in FIG. 7C.

In certain embodiments, sample 2130 can be exposed directly to a filtered ion beam 2150. By filtering the ion beam to achieve a narrower ion energy distribution, for example, the ion dose profile in sample 2130 is sharper following sample exposure than it would otherwise have been without filtering ion beam 2150. As a result, the width of the Bragg peak in sample 2130 is smaller relative to the Bragg peak width for an unfiltered ion beam. By exposing sample 2130 to a narrower distribution of incident ion energies, more refined control over the position of ion beam 2150 can be achieved; this level of ion exposure control can be useful when exposing various types of delicate sample materials.

Alternatively, the filtered ion beam can then be passed through one or more scattering elements and/or other devices to increase the width of the distribution of ion energies. This two-step approach to modifying the ion energy distribution—a first filtering step, followed by a second broadening step—can be used to produce ion energy distributions that are tailored for specific applications (e.g., specific to certain ion types and/or certain materials and/or certain pre-treatment conditions) that may not be achievable using a simpler one-step energy distribution broadening procedure.

As an example, by first filtering ion beam 2150, and then passing the filtered ion beam through one or more scattering elements 2170, the shape of the ion energy distribution can be made more Gaussian than would otherwise be possible using only a scattering step instead of the two-step procedure.

Ion filter 2210 can include one or more of a variety of different devices for removing ions from ion beam 2150. For example, in some embodiments, ion filter 2210 includes a hemispherical analyzer and aperture filter. The hemispherical analyzer includes a magnetic field source that disperses the ions of ion beam 2150 according to their kinetic energies. The aperture filter is then positioned in the path of the dispersed ion beam 2150 to permit only ions having a particular range of energies to pass through the aperture.

In certain embodiments, other devices can be used to filter ion beam 2150. For example, absorbing elements (e.g., elements configured to absorb incident ions having energies smaller than a selected energy threshold can be used to filter ion beam 2150. Suitable absorbing elements include metal foils, for example.

In some embodiments, ion beam 2150 (and in particular, the Bragg peak in an expected ion dose profile produced following exposure of sample 2130 to ion beam 2150) can be swept through sample 2130 to deliver selected radiation doses to various portions of the sample. In general, the position of the Bragg peak in sample 2130 can be selected by adjusting the average energy of ion beam 2150 (the average energy of ion beam 2150 typically corresponds to the maximum in the ion energy distribution). Ion source 2110, under the control of electronic controller 2190, can adjust the average energy of ion beam 2150 by changing an extraction voltage applied to accelerate ions in the ion source.

Figure 8:
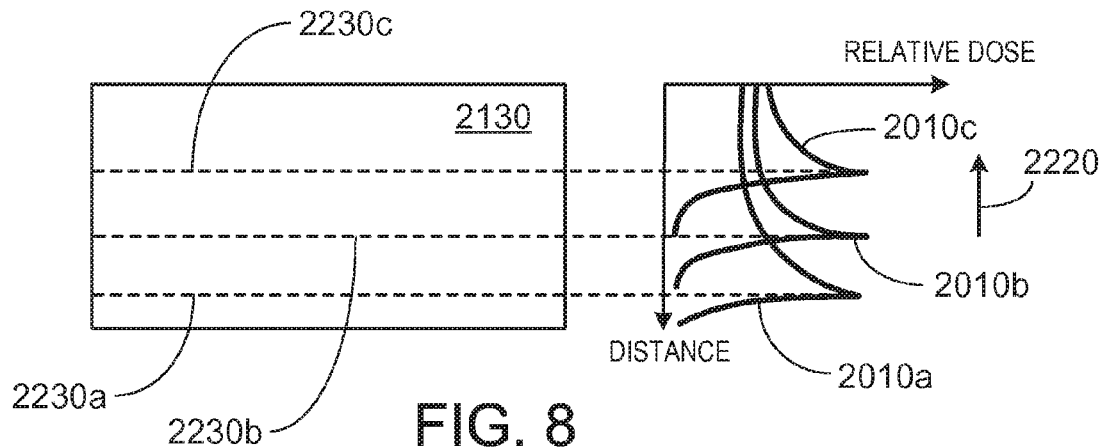
FIG. 8 is a schematic diagram showing three ion dose profiles corresponding to exposure of a sample to ion beams having different average energies.

FIG. 8 is a schematic diagram that shows how the Bragg peak of an ion dose profile in sample 2130 can be swept through the sample. As a first step, ion exposure system 2100 is configured to produce a first ion beam with a selected average ion energy corresponding to a particular extraction voltage applied in ion source 2110. When sample 2130 is exposed to the first ion beam, ion dose profile 2010a results in the sample, with the Bragg peak at position 2230a. Following exposure, the extraction voltage in ion source 2110 is adjusted to produce a second ion beam with a different average ion energy. When sample 2130 is exposed to the second ion beam, ion dose profile 2010b results in the sample. By further repeating the adjusting of the extraction voltage in ion source 2110 to produce additional beams with different average ion energies (and, therefore, different ion dose profiles, e.g., ion dose profile 2010c), and exposing sample 2130 to the additional beams, the Bragg peak of the ion dose profile can be swept through sample 2130 in the direction shown by arrow 2220, for example. More generally, however, by changing the extraction voltage in ion source 2110, the position of the Bragg peak in sample 2130 can be selected as desired, permitting delivery of large doses to selected regions of sample 2130 in any sequence.

In general, other properties of ion beam 2150 can also be adjusted in addition to, or as an alternative to, adjusting the average ion energy of the ion beam. For example, in some embodiments, the divergence angle of ion beam 2150 at the surface of sample 2130 can be adjusted to control the ion dose profile in sample 2130. Generally, by increasing the divergence angle of ion beam 2150 at the surface of sample 2130, the full width at half maximum of the Bragg peak in sample 2130 can be increased. Thus, in certain embodiments, the average energy of the ion beam can be maintained, but the ion dose profile in the material—including the position of the Bragg peak—can be changed by adjusting the ion beam's divergence angle.

The divergence angle can be adjusted automatically or by operator control by electronic controller 2190. Typically optical elements 2120 include one or more ion beam steering elements such as quadrupole and/or octopole deflectors. By adjusting potentials applied to the various electrodes of such deflectors, the divergence angle (and the angle of incidence) of ion beam 2150 at the surface of sample 2130 can be adjusted.

In some embodiments—unlike in other applications of ion beams such as surgical intervention—it can be advantageous to use ion beams with relatively large divergence angles, to ensure that the Bragg peak positioned in sample 2130 covers a suitable fraction of the thickness of sample 2130. For example, in certain embodiments, sample 2130 can be exposed to an ion beam having a divergence angle of 2 degrees or more (e.g., 5, 10, 15, 20, 30, 40, or even 50 degrees or more).

Figure 9A:
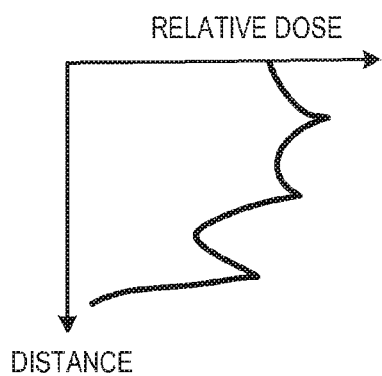
FIG. 9A is a schematic diagram showing a net ion dose profile for an exposed sample based on the three ion dose profiles of FIG. 8.

In some embodiments, both an ion beam current of ion beam 2150 and the average ion energy of ion beam 2150 can be adjusted to deliver a relatively constant dose as a function of thickness h of sample 2130. For example, if sample 2130 is exposed according to the sequential ion dose profiles 2010a, 2010b, and 2010c in FIG. 8, the net ion dose profile in sample 2130 corresponds to the sum of profiles 2010a-c, which is shown in FIG. 9A. Based on the net ion dose profile of FIG. 9A, it is evident that certain regions of sample 2130 receive larger net doses than other regions of sample 2130.

Figure 9B:
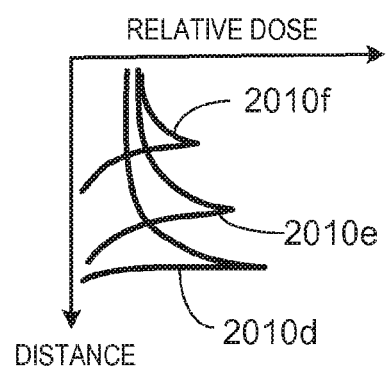
FIG. 9B is a schematic diagram showing three different ion dose profiles corresponding to ion beams of different average energy and ion current.
Figure 9C:
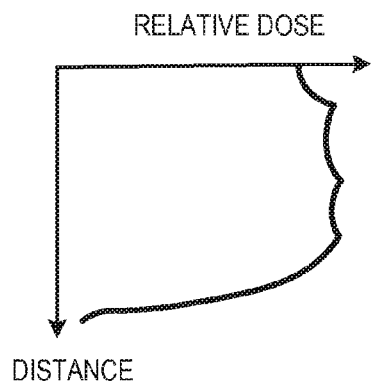
FIG. 9C is a schematic diagram showing a net ion dose profile based on the three ion dose profiles of FIG. 9B.

The differences in net dose can be reduced by adjusting the ion beam current of ion beam 2150 together with adjustments of the average ion energy. The ion beam current can be adjusted in ion source 2110 under the control of electronic controller 2190. For example, to reduce the difference in the net dose delivered to sample 2130 when the Bragg peak is swept through sample 2130 in the direction indicated by arrow 2220 in FIG. 8, the ion beam current can be successively reduced for each successive reduction in ion beam energy. Three ion dose profiles, each corresponding to successive decreases in both average ion energy and ion current in ion beam 2150, are shown as profiles 2010d-f, respectively, in FIG. 9B. The net ion dose profile in sample 2130 that results from these three sequential exposures is shown in FIG. 9C. The net ion dose profile shows significantly reduced variation as a function of position in sample 2130 relative to the net ion dose profile of FIG. 9A.

By carefully controlling the average energy and ion current of ion beam 2150, variations in net relative ion dose through the thickness of sample 2130 following exposure of the sample to ion beam 2150 can be relatively small. For example, a difference between a maximum net relative ion dose and a minimum net relative ion dose in sample 2130 following multiple exposures to ion beam 2150 can be 0.2 or less (e.g., 0.15, 0.1, 0.05, 0.04, 0.03, 0.02, 0.01 or even 0.005 or less).

By controlling the average energy and ion current of ion beam 2150, each portion of the exposed sample can receive a net dose of between 0.001 Mrad and 100 Mrad following multiple exposures to the ion beam (e.g., between 0.005 Mrad and 50 Mrad, between 0.01 Mrad and 50 Mrad, between 0.05 Mrad and 30 Mrad, between 0.1 Mrad and 20 Mrad, between 0.5 Mrad and 20 Mrad, or between 1 Mrad and 10 Mrad).

Figure 10A:
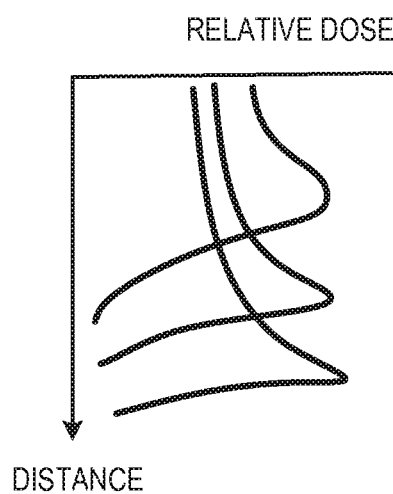
FIG. 10A is a schematic diagram showing three different ion dose profiles corresponding to exposure of a sample to beams of three different types of ions.
Figure 10B:
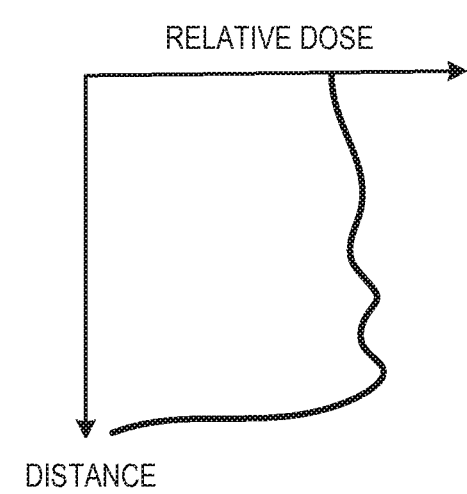
FIG. 10B is a schematic diagram showing a net ion dose profile based on the three ion dose profiles of FIG. 10A.

In some embodiments, sample 2130 can be exposed to different types of ions. Sample 2130 can be sequentially exposed to only one type of ion at a time, or the exposure of sample 2130 can include exposing sample 2130 to one or more ion beams that include two or more different types of ions. Different types of ions produce different ion dose profiles in an exposed material, and, by exposing a sample to different types of ions, a particular net ion dose profile in the sample can be realized. FIG. 10A shows a schematic diagram of three different ion dose profiles 2010g-i that result from exposing a sample 2130 to three different types of ions. Ion dose profiles 2010g-i can be produced via sequential exposure of the sample to each one of the different types of ions, or via concurrent exposure of the sample to two or even all three of the different types of ions. The net ion dose profile in sample 2130 that results from exposure to the three different types of ions is shown in FIG. 10B. Variations in the net ion dose profile as a function of thickness of the sample are reduced relative to any one of the individual ion dose profiles shown in FIG. 10A.

In some embodiments, the different types of ions can include ions of different atomic composition. For example, the different types of ions can include protons, carbon ions, oxygen ions, hydride ions, nitrogen ions, chlorine ions, fluorine ions, argon ions, neon ions, krypton ions, and various types of metal ions such as sodium ions, calcium ions, and lithium ions. Generally, any of these different types of ions can be used to treat sample 2130, and each will produce a different ion dose profile in a sample. In certain embodiments, ions can be generated from commonly available gases such as air. When air is used as a source gas, many different types of ions can be generated. The various different types of ions can be separated from one another prior to exposing sample 2130, or sample 2130 can be exposed to multiple different types of ions generated from a source gas such as air.

In some embodiments, the different types of ions can include ions having different charges. For example, the different types of ions can include various positive and/or negative ions. Further, the different types of ions can include ions having single and/or multiple charges. In general, positive and negative ions of the same chemical species can produce different ion dose profiles in a particular sample, and ions of the same chemical species that have different charge magnitudes (e.g., singly-charged, doubly-charged, triply-charged, quadruply-charged) can produce different ion dose profiles in a particular sample. By exposing a sample to multiple different types of ions, the change in the sample, e.g., sample breakdown (e.g., depolymerization, chain scission, and/or molecular weight reduction), functionalization, or other structural change, can be carefully and selectively controlled.

In some embodiments, the ion beam exposure system can adjust the composition of the ion beam based on the sample material. For example, certain types of sample, such as cellulosic biomass, include a large concentration of hydroxyl moieties. Accordingly, the effective penetration depth of certain types of ions—particularly protons—in such materials can be considerably larger than would otherwise be expected based on ion energy alone. Site-to-site proton hopping and other similar atomic excursions can significantly increase the mobility of such ions in the sample, effectively increasing the penetration depth of the incident ions. Further, the increased mobility of the ions in the sample can lead to a broadening of the Bragg peak. The ion beam exposure system can be configured to select particular types of ions for exposure of certain samples, accounting for the chemical and structural features of the sample. Further, the ion beam exposure system can be configured to take into account the expected interactions between the ion beam and the material when determining how to modify other parameters of the ion beam such as the distribution of ion energies therein.

An important aspect of the ion beam systems and methods disclosed herein is that the disclosed systems and methods enable exposure of biomass to ions in the presence of one or more additional fluids (e.g., gases and/or liquids). Typically, for example, when a material is exposed to an ion beam, the exposure occurs in a reduced pressure environment such as a vacuum chamber. The reduced pressure environment is used to reduce or prevent contamination of the exposed material, and also to reduce or prevent scattering of the ion beam by gas molecules. Unfortunately, ion beam exposure of materials in closed environments such as a vacuum chamber greatly restricts potential throughput for high volume material processing, however.

In the systems and methods disclosed herein, it has been recognized that exposure of biomass to an ion beam in the presence of one or more additional fluids can increase the efficiency of the biomass treatment. Additionally, exposure of biomass to an ion beam in an open environment (e.g., in air at normal atmospheric pressure) provides for much higher throughput than would otherwise be possible in a reduced pressure environment.

As discussed above, in some embodiments, biomass is exposed to an ion beam in the presence of a fluid such as air.

Ions accelerated in any one or more of the types of accelerators disclosed herein (or another type of accelerator) are coupled out of the accelerator via an output port (e.g., a thin membrane such as a metal foil), pass through a volume of space occupied by the fluid, and are then incident on the biomass material. In addition to directly treating the biomass, some of the ions generate additional chemical species by interacting with fluid particles (e.g., ions and/or radicals generated from various constituents of air). These generated chemical species can also interact with the biomass, and can act as initiators for a variety of different chemical bond-breaking reactions in the biomass (e.g., depolymerization and other chain-scission reactions).

In certain embodiments, additional fluids can be selectively introduced into the path of an ion beam before the ion beam is incident on the biomass. As discussed above, reactions between the ions and the particles of the introduced fluids can generate additional chemical species which react with the biomass and can assist in reducing the molecular weight of the biomass, and/or otherwise selectively altering certain properties of the biomass. The one or more additional fluids can be directed into the path of the ion beam from a supply tube, for example. The direction (i.e., fluid vector) and flow rate of the fluid(s) that is/are introduced can be selected according to a desired exposure rate and/or direction to control the efficiency of the overall biomass treatment, including effects that result from both ion-based treatment and effects that are due to the interaction of dynamically generated species from the introduced fluid with the biomass. In addition to air, exemplary fluids that can be introduced into the ion beam include oxygen, nitrogen, one or more noble gases, one or more halogens, and hydrogen.

In some embodiments, ion beams that include more that one different type of ions can be used to treat biomass. Beams that include multiple different types of ions can be generated by combining two or more different beams, each formed of one type of ion. Alternatively, or in addition, in certain embodiments, ion beams that include multiple different types of ions can be generated by introducing a multicomponent supply gas into an ion source and/or accelerator. For example, a multicomponent gas such as air can be used to generate an ion beam having different types of ions, including nitrogen ions, oxygen ions, argon ions, carbon ions, and other types of ions. Other multicomponent materials (e.g., gases, liquids, and solids) can be used to generate ion beams having different compositions. Filtering elements (e.g., hemispherical electrostatic filters) can be used to filter out certain ionic constituents and/or neutral species to selectively produce an ion beam having a particular composition, which can then be used to treat biomass. By using air as a source for producing ion beams for biomass treatment, the operating costs of a treatment system can be reduced relative to systems that rely on pure materials, for example.

Certain types of biomass materials may be particularly amenable to treatment with multiple different types of ions and/or multiple different processing methods. For example, cellulosic materials typically include crystalline polymeric cellulose chains which are cross-linked by amorphous hemicellulose fraction. The cellulose and hemicellulose is embedded within an amorphous lignin matrix. Separation of the cellulose fraction from the lignin and the hemicellulose using conventional methods is difficult and can be energy-intensive.

However, cellulosic biomass can be treated with multiple different types of ions to break down and separate the various components therein for further processing. In particular, the chemical properties of various types of ionic species can be used to process cellulosic biomass (and other types of biomass) to selectively degrade and separate the components thereof. For example, positively charged ions—and in particular, protons—act as acids when exposed to biomass material. Conversely, negatively charged ions, particularly hydride ions, act as bases when exposed to biomass material. As a result, the chemical properties of these species can be used to target specific components of treated biomass.

When treating lignocellulosic biomass, for example, the lignin matrix typically decomposes in the presence of basic reagents. Accordingly, by first treating cellulosic biomass with basic ions such as hydride ions (or electrons) from an ion (electron) beam, the lignin fraction can be preferentially degraded and separated from the cellullose and hemicellulose fractions. Cellulose is relatively unaffected by such an ion treatment, as cellullose is typically stable in the presence of basic agents.

In addition to negative ion treatment (or as an alternative to negative ion treatment), the lignocellulosic biomass can be treated with one or more basic agents in solution to assist in separating the lignin. For example, treatment of the lignocellulosic biomass with a sodium bicarbonate solution can degrade and/or solubilize the lignin, enabling separation of the solvated and/or suspended lignin from the cellulose and hemicellulose fractions.

Negative ion treatment with an ion beam may also assist in separating hemicellulose, which is also chemically sensitive to basic reagents. Depending upon the particular structure of the cellulosic biomass, more than treatment with negative ions may be used (and/or may be necessary) to effectively separate the hemicellulose fraction from the cellulose fraction. In addition, more that one type of ion can be used to separate the hemicellulose. For example, a relatively less basic ion beam such as an oxygen ion beam can be used to treat cellulosic biomass to degrade and/or remove the lignin fraction. Then, a stronger basic ion beam such as a hydride ion beam can be used to degrade and separate the hemicellulose from the cellulose. The cellulosic fraction remains largely unchanged as a result of exposure to two different types of basic ions.

However, the cellulose fraction decomposes in the presence of acidic agents. Accordingly, a further processing step can include exposing the cellulose fraction to one or more acidic ions such as protons from an ion beam, to assist in depolymerizing and/or degrading the cellulose fraction.

Each of the ion beam pretreatments and methods disclosed herein can be used in combination with other processing steps. For example, separation steps (including introducing a solvent such as water) can be used to wash away particular fractions of the cellulosic biomass as they are degraded. Additional chemical agents can be added to assist in separating the various components. For example, it has been observed that lignin that is separated from the cellulose and hemicellulose fractions can be suspended in a washing solution. However, the lignin can readily re-deposit from the solution onto the cellulose and hemicellulose fractions. To avoid re-deposition of the lignin, the suspension can be gently heated to ensure that the lignin remains below its glass transition temperature, and therefore remains fluid. By maintaining the lignin below its glass transition temperature, the lignin can be more readily washed out of cellulosic biomass. In general, heating of the suspension is carefully controlled to avoid thermal degradation of the sugars in the cellulosic fraction.

In addition, other treatment steps can be used to remove lignin from cellulose and hemicellulose. For example, in certain embodiments, lignocellulosic biomass can first be treated with relatively heavy ions (e.g., carbon ions, oxygen ions) to degrade lignin, and the cellulose and hemicellulose can then be treated with relatively light ions (e.g., protons, helium ions) and/or electrons to cause degradation of the cellulose and/or hemicellulose.

In some embodiments, one or more functionalizing agents can be added to the suspension containing the lignin to enhance the solubility of lignin in solution, thereby discouraging re-deposition on the cellulose and hemicellulose fractions. For example, agents such as ammonia gas and/or various types of alcohols can be used (to introduce amino and hydroxyl/alkoxy groups, respectively) to functionalize the lignin.

In certain embodiments, structural agents can be added to the lignin suspension to prevent re-deposition of the lignin onto the cellulose and hemicellulose fractions. Typically, when lignin forms a matrix surrounding cellulose and/or hemicellulose, the lignin adopts a heavily folded structure which permits relatively extensive van der Waals interactions with cellulose and hemicellulose. In contrast, when lignin is separated from cellulose and hemicellulose, the lignin adopts a more open, unfolded structure. By adding one or more agents that assist in preventing lignin re-folding to the lignin suspension, re-association of the lignin with cellulose and hemicellulose can be discouraged, and the lignin can be more effectively removed via washing, for example.

In some embodiments, no chemicals, e.g., no swelling agents, are added to the biomass prior to irradiation. For example, alkaline substances (such as sodium hydroxide, potassium hydroxide, lithium hydroxide and ammonium hydroxides), acidifying agents (such as mineral acids (e.g., sulfuric acid, hydrochloric acid and phosphoric acid)), salts, such as zinc chloride, calcium carbonate, sodium carbonate, benzyltrimethylammonium sulfate, or basic organic amines, such as ethylene diamine, may or may not be added prior to irradiation or other processing. In some cases, no additional water is added. For example, the biomass prior to processing can have less than 0.5 percent by weight added chemicals, e.g., less than 0.4, 0.25, 0.15 or 0.1 percent by weight added chemicals. In some instances, the biomass has no more than a trace, e.g., less than 0.05 percent by weight added chemicals, prior to irradiation. In other instances, the biomass prior to irradiation has substantially no added chemicals or swelling agents. Avoiding the use of such chemicals can also be extended throughout processing, e.g., at all times prior to fermentation, or at all times.

The various ion beam pretreatment methods disclosed herein can be used cooperatively with other pretreatment techniques such as sonication, electron beam irradiation, electromagnetic irradiation, steam explosion, chemical methods, and biological methods. Ion beam techniques provide significant advantages, including the ability to perform ion beam exposure of dry samples, to deliver large radiation doses to samples in short periods of time for high throughput applications, and to exercise relatively precise control over exposure conditions.

Quenching and Controlled Functionalization

After treatment with ionizing radiation, the materials described herein become ionized; that is, they include radicals at levels that are detectable with an electron spin resonance spectrometer. The current practical limit of detection of the radicals is about $10^{14}$ spins at room temperature. After ionization, any material that has been ionized can be quenched to reduce the level of radicals in the ionized material, e.g., such that the radicals are no longer detectable with the electron spin resonance spectrometer. For example, the radicals can be quenched by the application of a sufficient pressure to the material and/or by utilizing a fluid in contact with the ionized material, such as a gas or liquid, that reacts with (quenches) the radicals. The use of a gas or liquid to at least aid in the quenching of the radicals also allows the operator to control functionalization of the ionized material with a desired amount and kind of functional groups, such as carboxylic acid groups, enol groups, aldehyde groups, nitro groups, nitrile groups, amino groups, alkyl amino groups, alkyl groups, chloroalkyl groups or chlorofluoroalkyl groups. In some instances, such quenching can improve the stability of some of the ionized materials. For example, quenching can improve the resistance of the material to oxidation. Functionalization by quenching can also improve the solubility of the materials described herein, can improve the thermal stability of a material, and can improve material utilization by various microorganisms. For example, the functional groups imparted to a biomass material by quenching can act as receptor sites for attachment by microorganisms, e.g., to enhance cellulose hydrolysis by various microorganisms.

Thus, a molecular and/or a supramolecular structure of a feedstock can be changed by pretreating the feedstock with ionizing radiation, such as with electrons or ions of sufficient energy to ionize the feedstock, to provide a first level of radicals. If an ionized feedstock remains in the atmosphere, it will be oxidized, for example causing carboxylic acid groups to be generated by reacting with the atmospheric oxygen. In some instances with some materials, such oxidation is desired because it can aid in further breakdown in molecular weight, for example of a carbohydrate-containing biomass, and the oxidation groups, e.g., carboxylic acid groups, can be helpful for solubility and microorganism utilization. However, since the radicals can "live" for some time after irradiation, e.g., longer than 1 day, 5 days, 30 days, 3 months, 6 months or even longer than 1 year, material properties can continue to change over time, which in some instances, can be undesirable. Detecting radicals in irradiated samples by electron spin resonance spectroscopy and radical lifetimes in such samples is discussed in Bartolotta et al., Physics in Medicine and Biology, 46 (2001), 461-471 and in Bartolotta et al., Radiation Protection Dosimetry, Vol. 84, Nos. 1-4, pp. 293-296 (1999). The ionized material can be quenched to functionalize and/or to stabilize it. At any point, e.g., when the material is "alive", "partially alive" or fully quenched, the material can be converted into a product, e.g., a fuel, a food, or a composite.

In some embodiments, the quenching includes an application of pressure, such as by mechanically deforming the material, e.g., directly mechanically compressing the material in one, two, or three dimensions, or applying pressure to a fluid in which the material is immersed, e.g., isostatic pressing. In such instances, the deformation of the material itself brings radicals, which are often trapped in crystalline domains, in sufficient proximity so that the radicals can recombine, or react with another group. In some instances, the pressure is applied together with the application of heat, such as a sufficient quantity of heat to elevate the temperature of the material to above a melting point or softening point of a component of the material, such as lignin, cellulose or hemicellulose in the case of a biomass material. Heat can improve molecular mobility in the material, which can aid in the quenching of the radicals. When pressure is utilized to quench, the pressure can be greater than about 1000 psi, such as greater than about 1250 psi, 1450 psi, 3625 psi, 5075 psi, 7250 psi, 10000 psi or even greater than 15000 psi.

In some embodiments, quenching includes contacting the material with a fluid, such as a liquid or gas, e.g., a gas capable of reacting with the radicals, such as acetylene or a mixture of acetylene in nitrogen, ethylene, chlorinated ethylenes or chlorofluoroethylenes, propylene or mixtures of these gases. In other particular embodiments, quenching includes contacting the material, e.g., biomass, with a liquid, e.g., a liquid soluble in, or at least capable of penetrating into the biomass and reacting with the radicals, such as a diene, such as 1,5-cyclooctadiene. In some specific embodiments, the quenching includes contacting the biomass with an antioxidant, such as Vitamin E. If desired, the feedstock can include an antioxidant dispersed therein, and the quenching can come from contacting the antioxidant dispersed in the feedstock with the radicals.

Other methods for quenching are possible. For example, any method for quenching radicals in polymeric materials described in Muratoglu et al., U.S. Patent Application Publication No. 2008/0067724 and Muratoglu et al., U.S. Pat. No. 7,166,650, can be utilized for quenching any ionized material described herein. Furthermore any quenching agent (described as a "sensitizing agent" in the above-noted Muratoglu disclosures) and/or any antioxidant described in either Muratoglu reference can be utilized to quench any ionized material.

Functionalization can be enhanced by utilizing heavy charged ions, such as any of the heavier ions described herein. For example, if it is desired to enhance oxidation, charged oxygen ions can be utilized for the irradiation. If nitrogen functional groups are desired, nitrogen ions or ions that includes nitrogen can be utilized. Likewise, if sulfur or phosphorus groups are desired, sulfur or phosphorus ions can be used in the irradiation.

In some embodiments, after quenching any of the quenched materials described herein can be further treated with one or more of radiation, such as ionizing or non-ionizing radiation, sonication, pyrolysis, and oxidation for additional molecular and/or supramolecular structure change.

In particular embodiments, functionalized materials described herein are treated with an acid, base, nucleophile or Lewis acid for additional molecular and/or supramolecular structure change, such as additional molecular weight breakdown. Examples of acids include organic acids, such as acetic acid and mineral acids, such as hydrochloric, sulfuric and/or nitric acid. Examples of bases include strong mineral bases, such as a source of hydroxide ion, basic ions, such as fluoride ion, or weaker organic bases, such as amines. Even water and sodium bicarbonate, e.g., when dissolved in water, can effect molecular and/or supramolecular structure change, such as additional molecular weight breakdown.

The functionalized materials can be used as substrate materials to immobilize microorganisms and/or enzymes during bioprocessing, for example as described in U.S. Provisional Application Ser. Nos. 61/180,032 and 61/180,019, the disclosures of which are incorporated herein by reference.

Other embodiments are within the scope of the following claims. For example, non-biomass materials and mixtures of biomass materials and non-biomass materials can be processed using the methods described herein. Examples of non-biomass materials that can be processed include hydrocarbon-containing materials such as oil sands, oil shale, tar sands, bitumen, coal, and other such mixtures of hydrocarbons and non-hydrocarbon materials. Many other biomass and non-biomass materials can be processed using the methods described herein, including peat, lignin, pre-coal, and petrified and/or carbonized materials.

What is claimed is:

1. A method of changing a molecular structure of hydrocarbon-containing material, the method comprising:
   exposing a hydrocarbon-containing material to an ion beam comprising an adjusted distribution of ion energies, the distribution having been adjusted based, at least in part, on an expected ion dose profile resulting from exposing the hydrocarbon-containing material to the ion beam to cause chain scission of the hydrocarbon-containing material;
   wherein the hydrocarbon-containing material is selected from the group consisting of oil sands, oil shale, tar sands, bitumen, and coal.

2. The method of claim 1, wherein the adjustment of the distribution is based, at least in part, on a thickness of the hydrocarbon-containing containing material.

3. The method of claim 1, wherein prior to having been adjusted, the distribution of ion energies comprises a first distribution of ion energies having a full width at half maximum of W, and wherein the adjusted distribution of ion energies comprises a second distribution of ion energies having a full width at half maximum of more than W.

4. The method of claim 3, wherein the full width at half maximum of the second distribution is larger than W by a factor of 2.0 or more.

5. The method of claim 1, wherein the distribution having been adjusted comprises at least some ions having been directed to pass through a scattering element and/or a hemispherical analyzer.

6. The method of claim 1, wherein the ion beam passes through a fluid prior to being incident on the hydrocarbon-containing material.

7. The method of claim 6, wherein the fluid comprises air at a pressure of 0.5 atmospheres or more.

8. The method of claim 1, wherein the ion beam comprises two or more different types of ions from different atomic elements.

9. The method of claim 8, wherein the ion beam comprises: hydrogen ions and carbon ions; or hydrogen ions and oxygen ions.

10. The method of claim 1, wherein the distribution having been adjusted comprises at least some ions having been directed to pass through a scattering element configured to increase the full width at half maximum of the distribution of ion.

11. The method of claim 1, wherein the distribution having been adjusted comprises at least a portion of the ion beam having been filtered to remove at least some ions.

12. The method of claim 11, wherein at least a portion of the ion beam having been filtered comprises said portion having been directed to pass through a metal foil or a hemispherical analyzer.

13. The method of 11, wherein prior to having been filtered, the ion beam comprises a most probable energy E, and wherein at least a portion of the ion beam having been filtered comprises removing at least some ions having an energy less than E from the ion beam.

14. The method of claim 1, wherein the expected ion dose profile comprises an expected full width at half maximum of a Bragg peak.

15. The method of claim 14, wherein the distribution having been adjusted comprises increasing the expected full width at half maximum of a Bragg peak by an amount effective to reduce a difference between a thickness of the hydrocarbon-containing material and the full width at half maximum of a Bragg peak in the ion dose profile resulting from exposing the hydrocarbon-containing material to the ion beam.

16. The method of claim 14, wherein the difference between the thickness of the hydrocarbon-containing material and the full width at half maximum of a Bragg peak in the ion dose profile resulting from exposing the hydrocarbon-containing material to the ion beam is 0.01 centimeter or less.

17. The method of claim 1, wherein exposing the hydrocarbon-containing material to an ion beam comprising an adjusted distribution of ion energies comprises:
producing a first ion beam from an ion source, the first ion beam having a first average ion energy;
exposing the hydrocarbon-containing material to the first ion beam;
adjusting the ion source to produce a second ion beam having a second average ion energy different from the first average ion energy; and
exposing the hydrocarbon-containing material to the second ion beam.

18. The method of claim 17, wherein the first ion beam has a first average ion energy corresponding to a first position of a Bragg peak in an expected ion dose profile resulting from exposing the hydrocarbon-containing material to the first ion beam, and the second ion beam has a second average ion energy corresponding to a second position of a Bragg peak in an expected ion dose profile resulting from exposing the hydrocarbon-containing material to the second ion beam, the second position being different from the first position.

19. The method of claim 1, wherein the ion beam has a divergence angle of 10 degrees or more from an incident surface of the hydrocarbon-containing material.

20. The method of claim 1, wherein the distribution having been adjusted comprises an ion source having been adjusted to produce an ion beam having an average ion current and an average ion energy.

21. The method of claim 1, wherein the ion beam imparts a radiation dose to the hydrocarbon-containing material ranging from 0.01 Mrad to 50 Mrad.

22. The method of claim 1, further comprising exposing the hydrocarbon-containing material to a plurality of electrons or to ultrasonic energy.

23. The method of claim 1, wherein the ion beam comprises two or more different types of ions, the ions being from the same atomic element but bearing different charges.

24. A method of changing a molecular structure of a cellulosic or lignocellulosic material, the method comprising:
producing an ion beam comprising a first distribution of ion energies having a full width at half maximum of W;
adjusting the energies of at least some of the ions to produce a second distribution of ion energies in the ion beam having a full width at half maximum of more than W, said adjusting based, at least in part, on an expected ion dose profile resulting from exposing the cellulosic or lignocellulosic material to the ion beam; and
exposing the material to the ion beam to cause chain scission of the material.

25. The method of claim 24, wherein said adjusting is based, at least in part, on a thickness of the material.

26. The method of claim 25, wherein the fluid comprises air at a pressure of 0.5 atmospheres or more.

27. The method of claim 24, wherein the full width at half maximum of the second distribution is larger than W by a factor of 2.0 or more, or larger than W by a factor of 4.0 or more.

28. The method of claim 24, wherein adjusting the energies of at least some of the ions comprises directing the ions to pass through a scattering element or through a hemispherical analyzer.

29. The method of claim 24, wherein the ion beam passes through a fluid prior to being incident on the material.

30. The method of claim 24, wherein the ion beam comprises two or more different types of ions.

31. The method of claim 24, wherein the ion beam comprises: hydrogen ions and carbon ions; or hydrogen ions and oxygen ions.

32. The method of claim 24, wherein adjusting the energies of at least some of the ions comprises increasing an expected full width at half maximum of a Bragg peak of an expected ion dose profile in the material by an amount effective to reduce a difference between a thickness of the material and the full width at half maximum of a Bragg peak in the ion dose profile resulting from exposing the material to the ion beam.

33. The method of claim 32, wherein the difference between the thickness of the material and the full width at half maximum of a Bragg peak in the ion dose profile resulting from exposing the material to the ion beam is 0.01 centimeter or less.

* * * * *